US012604930B2

(12) United States Patent
Matsumoto et al.

(10) Patent No.: US 12,604,930 B2
(45) Date of Patent: Apr. 21, 2026

(54) NON-BURNING TYPE FLAVOR INHALER AND CONTROL METHOD

(71) Applicant: JAPAN TOBACCO INC., Tokyo (JP)

(72) Inventors: Hirofumi Matsumoto, Tokyo (JP); Akihiko Suzuki, Tokyo (JP); Manabu Takeuchi, Tokyo (JP); Takuma Nakano, Tokyo (JP); Masafumi Tarora, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 1073 days.

(21) Appl. No.: 17/110,893

(22) Filed: Dec. 3, 2020

(65) Prior Publication Data

US 2021/0084964 A1      Mar. 25, 2021

Related U.S. Application Data

(60) Division of application No. 15/590,385, filed on May 9, 2017, now Pat. No. 10,881,131, which is a (Continued)

(30) Foreign Application Priority Data

Nov. 10, 2014    (WO) .................. PCT/JP2014/079775

(51) Int. Cl.
*A24F 40/50*          (2020.01)
*A24B 15/167*        (2020.01)
(Continued)

(52) U.S. Cl.
CPC ............ *A24F 40/46* (2020.01); *A24B 15/167* (2016.11); *A24F 40/30* (2020.01); *A24F 40/50* (2020.01);
(Continued)

(58) Field of Classification Search
None
See application file for complete search history.

(56) References Cited

U.S. PATENT DOCUMENTS

| | | | |
|---|---|---|---|
| 6,040,560 A | 3/2000 | Fleischhauer et al. | |
| 2011/0036346 A1 | 2/2011 | Cohen et al. | |

(Continued)

FOREIGN PATENT DOCUMENTS

| | | | |
|---|---|---|---|
| EP | 2979791 A1 | 2/2016 | |
| EP | 3138424 A1 | 3/2017 | |

(Continued)

OTHER PUBLICATIONS

Australian Examination Report dated Jan. 22, 2019, for Australian Application No. 2015347900.
(Continued)

*Primary Examiner* — Katherine A Will
(74) *Attorney, Agent, or Firm* — XSENSUS LLP

(57) ABSTRACT

This non-combusting flavor inhaler is provided with a control unit which, as an instruction to a battery, outputs to the battery a prescribed instruction instructing the battery that the amount of aerosol vaporized by a vaporizer unit should fall within a desired range. The control unit stops power supply from the battery to the vaporizer unit once a prescribed period has elapsed since the start of supplying power to the vaporizer unit. The prescribed period is shorter than the upper limit value of a standard puff period, which is derived from a statistic of the user's puff period.

19 Claims, 19 Drawing Sheets

1

20

10
NON-MOUTHPIECE END

30
MOUTHPIECE END

PREDETERMINED
DIRECTION A

Related U.S. Application Data continuation of application No. PCT/JP2015/080749, filed on Oct. 30, 2015.

(51) Int. Cl.

| | |
|---|---|
| *A24F 40/30* | (2020.01) |
| *A24F 40/46* | (2020.01) |
| *A24F 40/65* | (2020.01) |
| *A24F 47/00* | (2020.01) |
| *A61K 9/00* | (2006.01) |
| *H02J 7/70* | (2026.01) |
| *H05B 1/02* | (2006.01) |
| *H05B 3/00* | (2006.01) |
| *A24F 40/10* | (2020.01) |
| *A24F 40/20* | (2020.01) |

(52) U.S. Cl.
CPC .............. *A24F 40/65* (2020.01); *A24F 47/00* (2013.01); *A61K 9/007* (2013.01); *H02J 7/751* (2026.01); *H05B 1/0202* (2013.01); *H05B 3/0014* (2013.01); *A24F 40/10* (2020.01); *A24F 40/20* (2020.01)

(56) References Cited

U.S. PATENT DOCUMENTS

| | | | |
|---|---|---|---|
| 2013/0213419 | A1 | 8/2013 | Tucker et al. |
| 2013/0284192 | A1 | 10/2013 | Peleg |
| 2013/0340775 | A1 | 12/2013 | Juster et al. |
| 2014/0014125 | A1* | 1/2014 | Fernando ................ A24F 40/50 131/328 |
| 2014/0053856 | A1* | 2/2014 | Liu ......................... A24F 40/51 131/329 |
| 2014/0060554 | A1 | 3/2014 | Collett et al. |
| 2014/0096781 | A1* | 4/2014 | Sears ...................... A24F 40/50 131/328 |
| 2014/0251324 | A1* | 9/2014 | Xiang ..................... A24F 40/50 128/202.21 |
| 2014/0345635 | A1 | 11/2014 | Rabinowitz et al. |
| 2015/0245660 | A1 | 9/2015 | Lord |

FOREIGN PATENT DOCUMENTS

| | | | |
|---|---|---|---|
| JP | 2003-307557 | A | 10/2003 |
| JP | 3976345 | B2 | 9/2007 |
| JP | 2013-130197 | A | 7/2013 |
| JP | WO 2015/166952 | A1 | 11/2015 |
| WO | WO 2013/116658 | A1 | 8/2013 |
| WO | 2014/102091 | A1 | 7/2014 |
| WO | WO 2014/110119 | A1 | 7/2014 |
| WO | WO 2014/167463 | A1 | 10/2014 |

OTHER PUBLICATIONS

Australian Examination Report dated Mar. 8, 2018 for corresponding Application No. 2015347900.
Chinese Office Action and Search Report, dated Apr. 2, 2019, for Chinese Application No. 201580060852.2, with an English translation of the Chinese Office Action.
Eurasian Office Action for Eurasian Application No. 201791037, dated May 17, 2019, with English translation.
Eurasian Office Action for Eurasian Application No. 201791037, dated Nov. 26, 2018, with English translation.
Extended European Search Report, dated Jun. 21, 2018, for European Application No. 15859321.0.
International Search Report, issued in PCT/JP2015/080749, PCT/ISA/210, dated Jan. 12, 2016.
Japanese Decision of Refusal for Japanese Application No. 2016-558982, dated Nov. 6, 2018, with English translation.
Japanese Notification of Reasons for Refusal and English translation, dated Nov. 7, 2017, for Japanese Application No. 2016-558982.
Japanese Notification of Reasons for Refusal for Japanese Application No. 2016-558982, dated Apr. 17, 2018, with an English translation.
Korean Office Action for Korean Application No. 10-2017-7013421, dated Oct. 30, 2018, with English translation.
Korean Office Action, dated Apr. 26, 2018, for Korean Application No. 10-2017-7013421, along with an English translation.
Marian et al., "Reconciling Human Smoking Behavior and Machine Smoking Patterns: Implications for Understanding Smoking Behavior and the Impact on Laboratory Studies," Cancer Epidemiol Biomarkers Prev., vol. 18, No. 12; Dec. 2009, pp. 3305-3320 (31 pages total).
Nemeth-Coslett et al., "Determinants of Puff Duration in Cigarette Smokers: II," Pharmacology Biochemistry & Behavior, vol. 21, 1984, pp. 903-912.
Japanese Office Action for Japanese Application No. 2020-018803 , dated Mar. 12, 2021, with English translation.
Japanese Office Action issued May 2, 2024 in corresponding Japanese Patent Application No. 2023-029400, 6 pages.

* cited by examiner

NON-MOUTHPIECE END                    MOUTHPIECE END

PREDETERMINED
DIRECTION A

MOUTHPIECE END                    NON-MOUTHPIECE END

PREDETERMINED
DIRECTION A

UPSTREAM     PREDETERMINED DIRECTION A     DOWNSTREAM

UPSTREAM        PREDETERMINED        DOWNSTREAM
                 DIRECTION A

UPSTREAM          PREDETERMINED          DOWNSTREAM
                  DIRECTION A

UPSTREAM          PREDETERMINED          DOWNSTREAM
                  DIRECTION A

UPSTREAM     PREDETERMINED DIRECTION A     DOWNSTREAM

UPSTREAM     PREDETERMINED DIRECTION A     DOWNSTREAM

TPM AMOUNT
(mg/PUFF ACTION)

SAMPLE E2

}DESIRED RANGE

SAMPLE E1

Puff number

TPM AMOUNT
(mg/PUFF ACTION)

}DESIRED RANGE

SAMPLE F2

SAMPLE F1

Puff number

NON-BURNING TYPE FLAVOR INHALER AND CONTROL METHOD

CROSS-REFERENCE TO RELATED APPLICATIONS

This application is a Divisional of co-pending U.S. patent application Ser. No. 15/590,385 filed on May 9, 2017, which is a Continuation of PCT International Application No. PCT/JP2015/080749 filed on Oct. 30, 2015, which claims priority under 35 U.S.C. § 119(a) to Patent Application No. PCT/JP2014/079775 filed in Japan on Nov. 10, 2014, all of which are hereby expressly incorporated by reference into the present application.

TECHNICAL FIELD

The present invention relates to a non-burning type flavor inhaler that atomizes an aerosol source using power supplied from a battery and a control method used by the non-burning type flavor inhaler.

BACKGROUND ART

Known is a non-burning type flavor inhaler provided with an atomizer that atomizes an aerosol source using power supplied from a battery (for example, Patent Document 1).

PRIOR ART DOCUMENT

Patent Document

Patent Document 1: WO 2013/116558

SUMMARY OF THE INVENTION

A first feature is summarized as a non-burning type flavor inhaler comprising: an atomizer configured to atomize an aerosol source without burning; a battery configured to accumulate power supplied to the atomizer; and a controller configured to output a predetermined instruction to the battery as an instruction to the battery, the predetermined instruction instructing the battery to make an aerosol amount, atomized by the atomizer, falls within a desired range, wherein the controller stops power supply from the battery to the atomizer when a predetermined period elapses from starting the power supply to the atomizer, and wherein the predetermined period is shorter than an upper limit value of a standard puff period derived from statistics of a puff period of a user.

A second feature according to the first feature is summarized as that the atomizer is configured to be capable of atomizing the aerosol amount greater than the desired range in one puff action at least at a start of usage of the atomizer.

A third feature according to the first feature or the second feature is summarized as that the predetermined instruction is determined based on the length of the predetermined period such that the aerosol amount, atomized by the atomizer in the predetermined period, falls within the desired range.

A fourth feature according to any one of the first feature to the third feature is summarized as that the controller modifies the predetermined instruction with a reduction of an accumulated amount in the battery such that the aerosol amount atomized by the atomizer falls within the desired range.

A fifth feature according to any one of the first feature to the fourth feature is summarized as that the controller estimates an accumulated amount in the battery based on a voltage value output from the battery.

A sixth feature according to any one of the first feature to the fifth feature is summarized as that the controller controls the amount of power supplied from the battery to the atomizer by pulse control, and the controller, as a modification of the predetermined instruction, increases a duty ratio output to the battery in one puff action with a reduction of the accumulated amount in the battery such that the aerosol amount atomized by the atomizer falls within the desired range.

A seventh feature according to any one of the first feature to the sixth feature is summarized as that the controller, as a modification of the predetermined instruction, increases an instruction voltage output to the battery with the reduction of the accumulated amount in the battery such that the aerosol amount atomized by the atomizer falls within the desired range.

An eighth feature according to any one of the first feature to the seventh feature is summarized as that the atomizer is configured by a heating wire having a resistance value in a range from 1.0 to 3.0Ω.

A ninth feature according to any one of the first feature to the eighth feature is summarized as that the atomizer is configured by a heating wire wounded at a predetermined pitch, and the predetermined pitch is in a range of 0.40 mm or less.

A tenth feature according to any one of the first feature to the ninth feature is summarized as that an initial value of an output voltage of the battery is in a range from 1.2 to 4.2 V.

An eleventh feature according to any one of the first feature to the tenth feature is summarized as that battery capacity of the battery is in a range from 100 to 1000 mAh.

A twelfth feature according to any one of the first feature to the eleventh feature is summarized as that the predetermined period is shorter than an average value of a puff period derived from statistics of a puff period of a user.

A thirteenth feature according to any one of the first feature to the twelfth feature is summarized as that the predetermined period is one to three seconds.

A fourteenth feature according to any one of the first feature to the thirteenth feature is summarized as that the predetermined period is from 1.5 to 2.5 seconds.

A fifteenth feature according to any one of the first feature to the fourteenth feature is summarized as the non-burning type flavor inhaler comprising: a memory configured to store a puff period in which a user performs a puff action, wherein the predetermined period is derived from statistics based on the puff period stored in the memory.

A sixteenth feature according to the fifteenth is summarized as the non-burning type flavor inhaler comprising: a calculator configured to calculate the predetermined period from statistics based on the puff period stored in the memory.

A seventeenth feature according to the fifteenth is summarized as the non-burning type flavor inhaler comprising: an interface configured to communicate with an external device provided separately from the non-burning type flavor inhaler, wherein the interface transmits the puff period stored in the memory to the external device, and wherein the interface receives from the external device the predetermined period calculated from statistics based on the puff period using the external device.

An eighteenth feature according to any one of the first feature to the seventeenth feature is summarized as the non-burning type flavor inhaler comprising: a flavor source configured to impart flavor to aerosol atomized by the atomizer, wherein an upper limit of the desired range is 4.0 mg per one puff action, and wherein a lower limit of the desired range is 0.1 mg per one puff action.

A nineteenth feature according to any one of the first feature to the eighteenth feature is summarized as that the controller controls a light emitting element in a predetermined mode in a puff period in which a user performs a puff action, and the controller controls the light emitting element in the predetermined mode when the puff action continues even when power supply from the battery to the atomizer is stopped.

A twentieth feature according to the nineteenth feature is summarized as that wherein the controller controls a light emitting element in the predetermined mode during detection of a puff action of a user using an inhalation sensor.

A twenty-first feature is summarized as a control method, comprising the steps of (a) outputting a predetermined instruction to a battery as an instruction to the battery, the battery accumulating power supplied to an atomizer configured to atomize an aerosol source without burning, the predetermined instruction instructing the battery to make an aerosol amount, atomized by the atomizer, falls within the desired range; and (b) stopping power supply from the battery to the atomizer when a predetermined period elapses from a start of power supply to the atomizer, wherein the predetermined period is shorter than an upper limit value of a standard puff period derived from statistics of a puff period of a user.

A twenty-second feature according to the twenty-first feature is summarized as that the predetermined instruction is determined based on the length of the predetermined period such that the aerosol amount, atomized by the atomizer in the predetermined period, falls within the desired range.

A twenty-third feature according to the twenty-first feature or the twenty-second feature is summarized as that the step (a) includes modifying the predetermined instruction with a reduction of an accumulated amount in the battery such that the aerosol amount atomized by the atomizer falls within the desired range.

A twenty-fourth feature according to any one of the twenty-first feature to the twenty-third feature is summarized as that the predetermined period is derived from statistics based on a puff period stored in a memory configured to store a puff period in which a user performs a puff action.

DESCRIPTION OF THE EMBODIMENT

Figure 1:
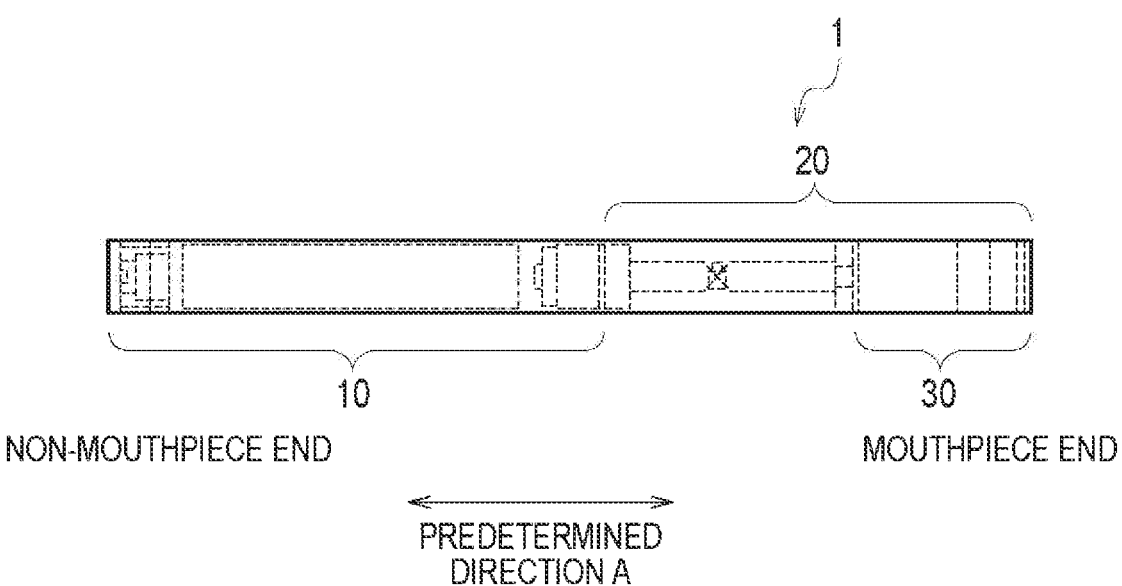
FIG. 1 is a cross-sectional view illustrating a non-burning type flavor inhaler 1 according to an embodiment.

Hereinafter, embodiments of the present invention will be described. In the following description of the drawings, the same or similar reference numerals denote the same or similar parts. It should be noted that the drawings are schematic, and the ratios of dimensions and the like may be different from the actual ones.

Therefore, specific dimensions and the like may be determined by referring to the following description. Of course, the drawings may include the parts having different dimensions and ratios.

Overview of Disclosure

In the non-burning type flavor inhaler mentioned in the background art, it is difficult to realize a non-burning type flavor inhaler in which an aerosol amount supplied per one puff action falls within a desired range through a puff action from the start of smoking (an initial stage in which an accumulated amount in a battery is sufficient) until the end of smoking (that is, a final stage in which the accumulated amount in the battery decreases) caused by a factor such as variance of a puff period of a user, and decrease of the accumulated amount in a battery, regardless of the length of the puff period of the user and the accumulated amount in the battery.

A non-burning type flavor inhaler according to the overview of disclosure comprises: an atomizer configured to atomize an aerosol source without burning; a battery configured to accumulate power supplied to the atomizer; and a controller configured to output a predetermined instruction to the battery as an instruction to the battery, the predetermined instruction instructing the battery to make an aerosol amount, atomized by the atomizer, falls within a desired range. The controller stops power supply from the battery to the atomizer when a predetermined period elapses from starting the power supply to the atomizer, and wherein the predetermined period is shorter than an upper limit value of a standard puff period derived from statistics of a puff period of a user.

In the overview of disclosure, the controller stops the power supply from the battery to the atomizer when the predetermined period elapses from starting the power supply to the atomizer. The predetermined period is shorter than the upper limit value of the standard puff period derived from statistics of puff periods of users. Accordingly, even if the non-burning type flavor inhaler is used by a user who has a puff period longer than the predetermined period, it is easy to suppress an extreme decrease of the accumulated amount in the battery and easy to control the predetermined instruction such that the aerosol amount atomized by the atomizer falls within the desired range.

As described above, it is possible to falls the aerosol amount supplied per one puff action in the desired range through a puff action from the start of smoking (the initial stage in which an accumulated amount in a battery is sufficient) until the end of smoking (that is, the final stage in which the accumulated amount in the battery decreases), regardless of the length of the puff period of the user and the accumulated amount in the battery.

Embodiment (Non-Burning Type Flavor Inhaler)

Figure 2:
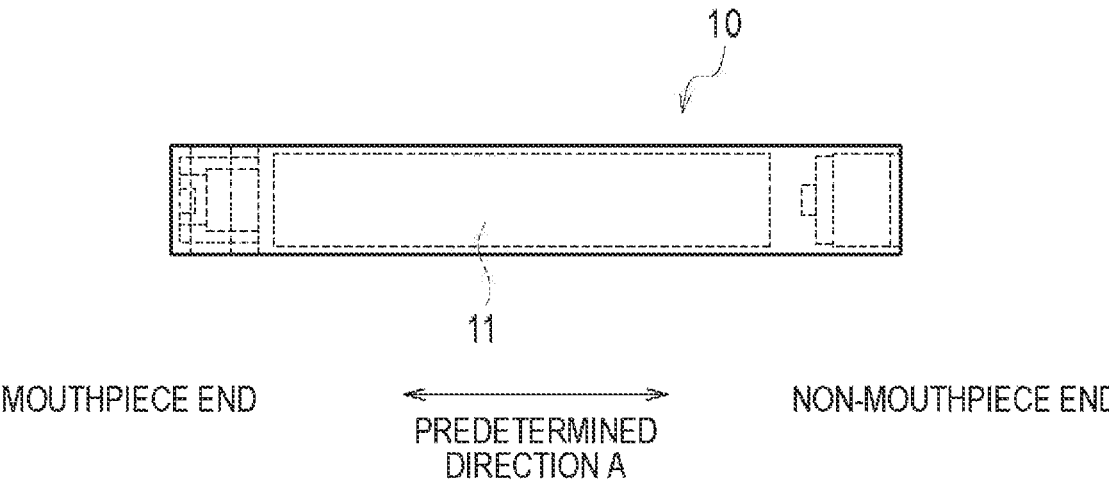
FIG. 2 is a cross-sectional view illustrating a power source unit 10 according to the embodiment.
Figure 3:
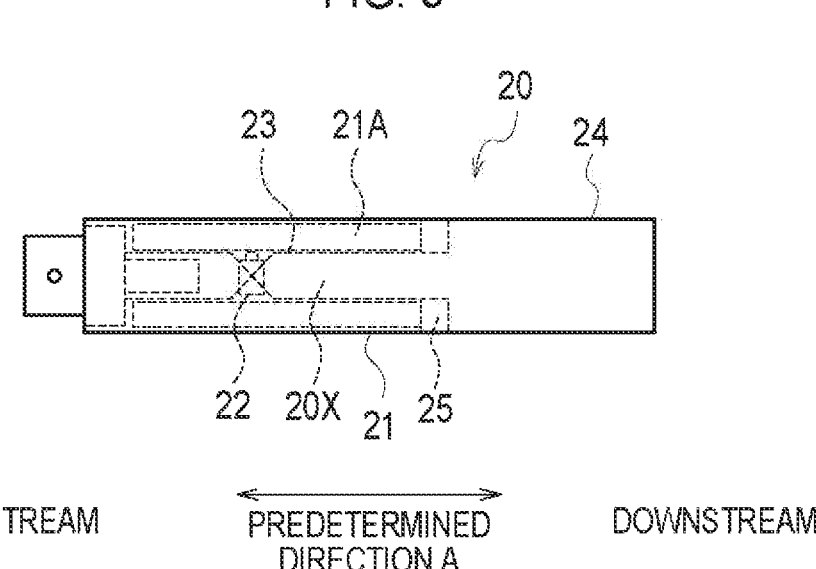
FIG. 3 is a cross-sectional view illustrating a first cartridge 20 according to the embodiment.
Figure 4:
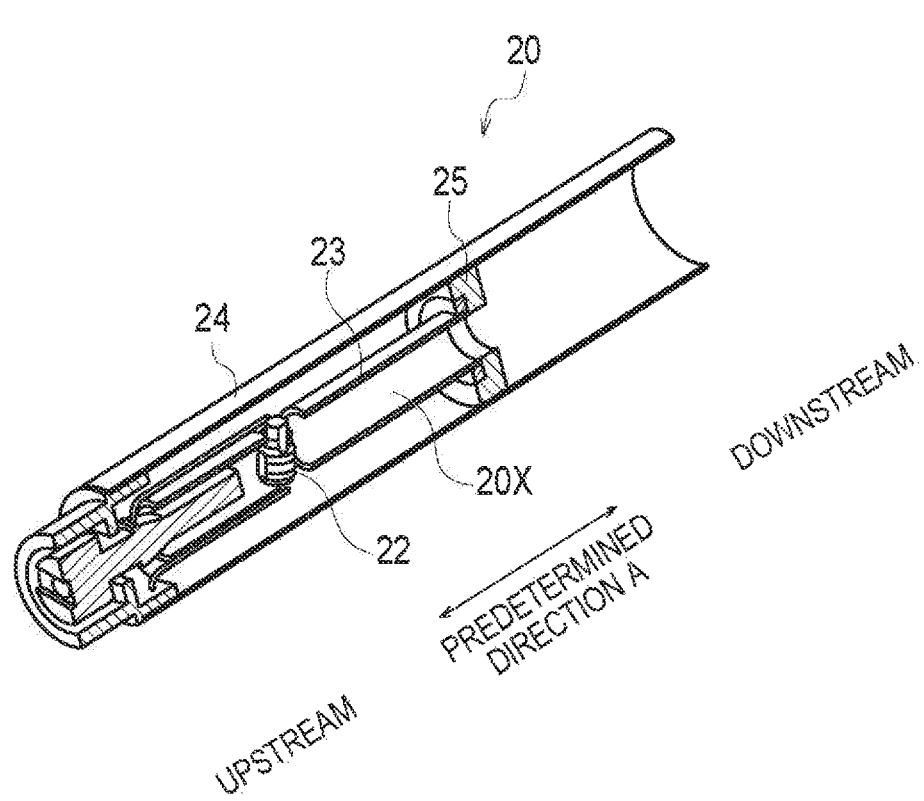
FIG. 4 is a diagram illustrating an internal structure of the first cartridge 20 according to the embodiment.
Figure 5:
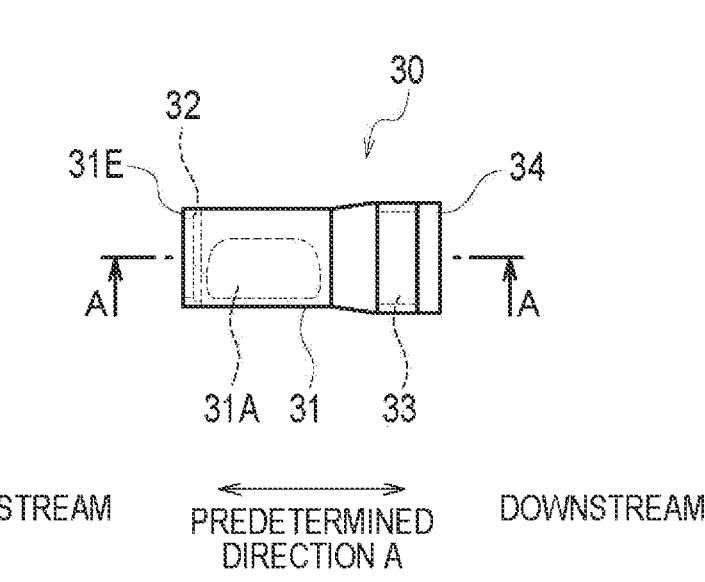
FIG. 5 is a cross-sectional view illustrating a second cartridge 30 according to the embodiment.
Figure 6:
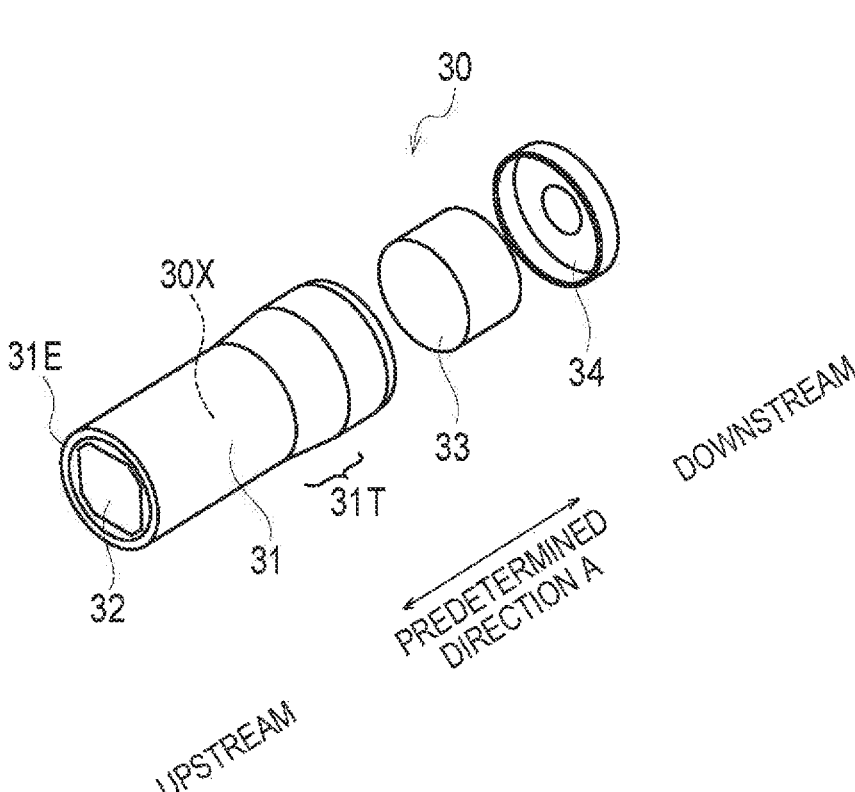
FIG. 6 is an exploded perspective view of the second cartridge 30 according to the embodiment.
Figure 7:
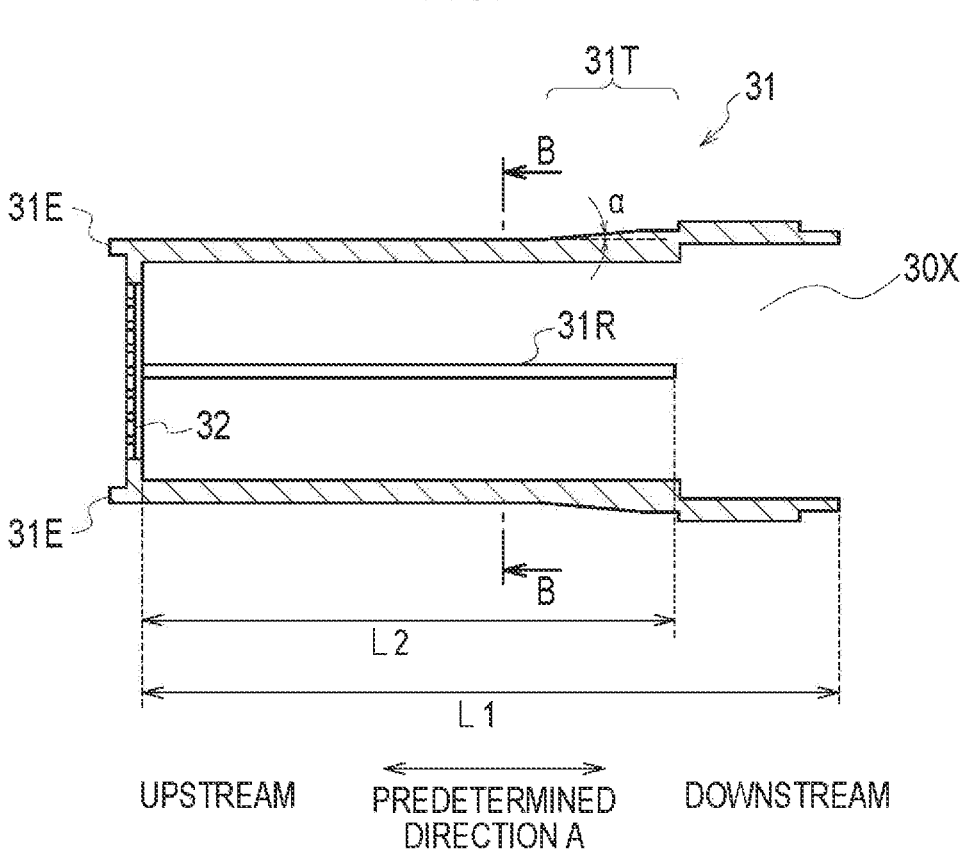
FIG. 7 is a cross-sectional view (cross-sectional view taken along A-A illustrated in FIG. 5) illustrating a flavor source container 31 according to the embodiment.
Figure 8:
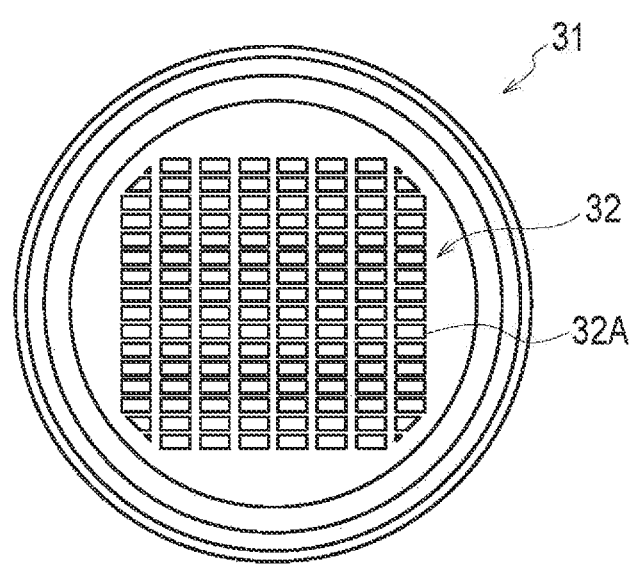
FIG. 8 is a cross-sectional view (cross-sectional view taken along B-B illustrated in FIG. 7) illustrating the flavor source container 31 according to the embodiment.

A non-burning type flavor inhaler according to an embodiment will be described below. FIG. 1 is a cross-sectional view illustrating a non-burning type flavor inhaler 1 according to the embodiment. FIG. 2 is a cross-sectional view illustrating a power source unit 10 according to the embodiment. FIG. 3 is a cross-sectional view illustrating a first cartridge 20 according to the embodiment. FIG. 4 is a diagram illustrating an internal structure of the first cartridge 20 according to the embodiment. It should be noted that a reservoir 21 that will be described later is omitted from FIG. 4. FIG. 5 is a side view illustrating a second cartridge 30 according to the embodiment. FIG. 6 is an exploded perspective view of the second cartridge 30 according to the embodiment. FIG. 7 is a cross-sectional view (cross-sectional view taken along A-A illustrated in FIG. 5) illustrating a flavor source container 31 according to the embodiment. FIG. 8 is a cross-sectional view (cross-sectional view taken along B-B illustrated in FIG. 7) illustrating the flavor source container 31 according to the embodiment. It should be noted that a flavor source 31A that will be described later is omitted from FIG. 6.

As illustrated in FIG. 1, the non-burning type flavor inhaler 1 has a shape extending in a predetermined direction A from a non-mouthpiece end toward a mouthpiece end. The non-burning type flavor inhaler 1 is an instrument for inhaling flavor without burning.

Specifically, the non-burning type flavor inhaler 1 has the power source unit 10, the first cartridge 20, and the second cartridge 30. The first cartridge 20 is attachable to and detachable from the power source unit 10, and the second cartridge 30 is attachable to and detachable from the first cartridge 20. In other words, the first cartridge 20 and the second cartridge 30 are each replaceable.

As illustrated in FIG. 2, the power source unit 10 has a shape extending along the predetermined direction A, and has at least a battery 11. The battery 11 may be a disposable battery and may be a rechargeable battery. An initial value of output voltage of the battery 11 is preferably in a range of from 1.2 to 4.2 V. In addition, the battery capacity of the battery 11 is preferably in a range of from 100 to 1000 mAh.

As illustrated in FIG. 3 and FIG. 4, the first cartridge 20 has a shape extending along the predetermined direction A. The first cartridge 20 has a reservoir 21, an atomizer 22, a flow path forming body 23, an outer frame 24, and an end cap 25. The first cartridge 20 has a first flow path 20X provided on the downstream than the atomizer 22 as an aerosol flow path extending along the predetermined direction A. It should be noted that in the aerosol flow path, a side near to the atomizer 22 is referred to as upstream and a side away from the atomizer 22 is referred to as downstream.

The reservoir 21 retains an aerosol source 21A. The reservoir 21 is positioned on the periphery of the flow path forming body 23 in a cross section orthogonal to the first flow path 20X (predetermined direction A). In the embodiment, the reservoir 21 is positioned in a gap between the flow path forming body 23 and the outer frame 24. For example, the reservoir 21 is constituted by a porous body such as a resin web or cotton. However, the reservoir 21 may be constituted by a tank that accommodates the liquid aerosol source 21A. The aerosol source 21A includes a liquid such as glycerin or propylene glycol.

The atomizer 22 atomizes the aerosol source 21A not accompanying burning caused by power supplied from the battery 11. In the embodiment, the atomizer 22 is constituted by a heating wire (coil) wound at a predetermined pitch, and preferably the atomizer 22 is constituted by a heating wire that has a resistance value in the range of from 1.0 to 3.0Ω. The predetermined pitch is a value or more such that the heating wires do not contact, and preferably is a small value. For example, the predetermined pitch is preferably 0.40 mm or less. The predetermined pitch is preferably fixed to stabilize atomization of the aerosol source 21A. Note that, the predetermined pitch is an interval in the center of heating wires that are adjacent to each other.

The flow path forming body 23 has a shape extending along the predetermined direction A. The flow path forming body 23 has a cylindrical shape that forms the first flow path 20X extending along the predetermined direction A.

The outer frame 24 has a shape extending along the predetermined direction A. The outer frame 24 has a cylindrical shape that accommodates the flow path forming body 23. In the embodiment, the outer frame 24 accommodates a part of the second cartridge 30 while extending to the downstream side than the end cap 25.

The end cap 25 is a cap that closes a gap between the flow path forming body 23 and the outer frame 24 from the downstream side. The end cap 25 suppresses a situation such that the aerosol source 21A retained in the reservoir 21 leaks to the second cartridge 30 side.

As illustrated in FIG. 5 and FIG. 6, the second cartridge 30 has at least the flavor source 31A. The second cartridge 30 is mounted in the non-burning type flavor inhaler 1. In the embodiment, the second cartridge 30 is connected to the first cartridge 20. More particularly, a part of the second cartridge 30 is accommodated in the outer frame 24 of the first cartridge 20 as described above.

The second cartridge 30 has a shape extending along the predetermined direction A. The second cartridge 30 has the flavor source container 31, a mesh body 32, a filter 33, and a cap 34. The second cartridge 30 has a second flow path 30X provided on the downstream than the first flow path 20X as the aerosol flow path.

The second cartridge 30 imparts flavor to the aerosol by letting the aerosol atomized by the atomizer 22 pass through. Here, in the embodiment, it should be noted that it is possible to impart flavor to the aerosol without heating the flavor source 31A. It should be noted that the aerosol is not practically generated from the flavor source 31A.

In the predetermined direction A, preferably a maximum size of the second cartridge 30 is 40 mm or less. Furthermore, in the predetermined direction A, preferably the maximum size of the second cartridge 30 is 25 mm or less. Meanwhile, in the predetermined direction A, preferably a minimum size of the second cartridge 30 is 5 mm or more. Furthermore, in the predetermined direction A, preferably the minimum size of the second cartridge 30 is 1 mm or more. In a direction orthogonal to the predetermined direction A, preferably the maximum size of the second cartridge 30 is 20 mm or less. Furthermore, in the direction orthogonal to the predetermined direction A, preferably the maximum size of the second cartridge 30 is 10 mm or less. Meanwhile, in the direction orthogonal to the predetermined direction A, preferably the minimum size of the second cartridge 30 is 3 mm or more. Furthermore, in the direction orthogonal to the predetermined direction A, preferably the minimum size of the second cartridge 30 is 1 mm or more.

The flavor source container 31 has a cylindrical shape and forms the second flow path 30X extending along the predetermined direction A. The flavor source container 31 accommodates the flavor source 31A. The flavor source 31A that imparts flavor to the aerosol is accommodated in the second flow path 30X. Here, in a cross section orthogonal to the aerosol flow path (predetermined direction A), preferably the size of the first flow path 20X is small to secure volume of the reservoir 21 that retains the aerosol source 21A. Accordingly, in a case in which the second cartridge 30 is accommodated in the outer frame 24 that has a fixed cross-sectional area across the aerosol flow path (predetermined direction A), as a result, the size of the second flow path 30X tends to be larger than the size of the first flow path 20X described above.

The flavor source 31A is constituted by raw material pieces that impart flavor to the aerosol generated by the non-burning type flavor inhaler 1. Preferably the lower limit of the size of the raw material pieces is from 0.2 to 1.2 mm. Furthermore, preferably the lower limit of the size of the raw material pieces is from 0.2 to 0.7 mm. The smaller the size of the raw material pieces included in the flavor source 31A, the more the specific surface area increases, therefore a flavor component tends to be released from the raw material pieces included in the flavor source 31A. It is possible to use shredded tobacco or a molded body in which a tobacco raw material is granularly formed as the raw material pieces included in the flavor source 31A. The flavor source 31A may be constituted by a plant other than tobacco (for example, mint and herbs). Flavorings such as menthol may be added to the flavor source 31A.

Here, for example, the raw material pieces included in the flavor source 31A are obtained by sieving compliant with JIS Z 8815 using a stainless steel sieve compliant with JIS Z 8801. For example, the raw material pieces that pass through the stainless steel sieve that has sieve openings of 0.71 mm are obtained by sieving the raw material pieces over 20 minutes by a drying and mechanical shaking method using the stainless steel sieve that has the sieve openings of 0.71 mm. Subsequently, the raw material pieces that pass through the stainless steel sieve that has sieve openings of 0.212 mm are removed by sieving the raw material pieces over 20 minutes by the drying and mechanical shaking method using the stainless steel sieve that has the sieve openings of 0.212 mm. That is, the raw material pieces included in the flavor source 31A are raw material pieces that pass through the stainless steel sieve (sieve openings=0.71 mm) that regulates the upper limit and do not pass through the stainless steel sieve (sieve openings=0.212 mm) that regulates the lower limit. Accordingly, in the embodiment, the lower limit of the size of the raw material pieces included in the flavor source 31A is defined by the sieve openings of the stainless steel sieve that regulates the lower limit. Note that, the upper limit of the size of the raw material pieces included in the flavor source 31A is defined by the sieve openings of the stainless steel sieve that regulates the upper limit.

In the embodiment, as illustrated in FIG. 6 and FIG. 7, preferably the flavor source container 31 has a protruding portion 31E that protrudes to the upstream side (in the embodiment, the flow path forming body 23 or the end cap 25 side) from an outer edge of an upstream end portion (here, the mesh body 32) of the flavor source container 31 in a cross section orthogonal to the aerosol flow path (predetermined direction A). The protruding portion 31E may be continuously provided along the outer edge of the upstream end portion (here, the mesh body 32) of the flavor source container 31 and may be intermittently provided along the outer edge of the flavor source container 31. Note that, when there is a gap between the outer frame 24 and the flavor source container 31, preferably the protruding portion 31E is continuously provided along the outer edge of the upstream end portion (here, the mesh body 32) of the flavor source container 31. Thereby, it is possible to suppress retention of aerosol in the gap formed in the upstream part of a taper part 31T.

In the embodiment, as illustrated in FIG. 6 and FIG. 7, preferably an outer wall surface of the flavor source container 31 includes the taper part 31T that becomes wide from the upstream to the downstream. The taper part 31T may be contained in a part of the outer wall surface of the flavor source container 31. For example, a taper angle α of the taper part 31T is approximately 5 degrees.

In the embodiment, as illustrated in FIG. 7, preferably a rib 31R extending along the predetermined direction A from the upstream to the downstream is provided in an inner wall surface of the flavor source container 31. Although not particularly limited, preferably the number of ribs 31R is two or more. Preferably the downstream end portion of the ribs 31R does not reach the downstream end portion of the flavor source container 31. For example, in the predetermined direction A, a length L2 from the mesh body 32 to the downstream end portion of the ribs 31R is shorter than a length L1 from the mesh body 32 to the downstream end portion of the flavor source container 31. In other words, in a state in which the filter 33 is inserted in the flavor source container 31, preferably the downstream end portion of the ribs 31R contacts the filter 33 without reaching the downstream end portion of the flavor source container 31.

The mesh body 32 is provided on the upstream (non-mouthpiece side) than the flavor source 31A. In the embodiment, the mesh body 32 is provided on the upstream end portion of the flavor source container 31. When the mesh body 32 provided in the flavor source container 31 is very small, from the perspective of securing strength of the mesh body 32, preferably the flavor source container 31 and the mesh body 32 are integrally formed. That is, in the embodiment, the mesh body 32 is a part of the flavor source container 31. In such a case, preferably the flavor source container 31 and the mesh body 32 are configured by resin. For example, it is possible to use one or more resins that are selected from polypropylene, polyethylene terephthalate, polyethylene resin, and ABS resin as the resin. From the perspective of moldability and texture, preferably the resin is polypropylene. The flavor source container 31 and the mesh body 32 are constituted by metallic molding or injection molding.

In the embodiment, as illustrated in FIG. 8, the mesh body 32 has a plurality of openings 32A. Each of the plurality of openings 32A has a polygon shape that has an internal angle of 180° or less. Each of the plurality of openings 32A has, as widths through which each center of gravity of the plurality of openings 32A passes, a minimum width Wmin having the smallest width and a maximum width Wmax having the largest width. The minimum width Wmin is smaller than the lower limit of the size of the raw material pieces included in the flavor source 31A. More particularly, since the raw material pieces that actually constitutes the flavor source 31A are non-spherical, from the perspective of suppressing drop out of the raw material pieces, preferably the minimum width Wmin is smaller than ½ the lower limit of the size of the raw material pieces included in the flavor source 31A. The maximum width Wmax is larger than the minimum width Wmin. For example, preferably the maximum width Wmax is larger than the lower limit of the size of the raw material pieces. Alternatively, preferably the maximum width Wmax is from √2 times to six times of the minimum width Wmin. That is, each of the plurality of openings 32A is a shape different from a circle. Furthermore, since the raw material pieces tend not to fit in the opening 32A, preferably each of the plurality of openings 32A is a rectangular shape. Note that, each side of the rectangular shape that the opening 32A may include a nonlinear part generated in manufacturing the opening 32A. In addition, each vertex of the rectangular shape that the opening 32A may include a curved part generated in manufacturing the opening 32A.

Figure 9:
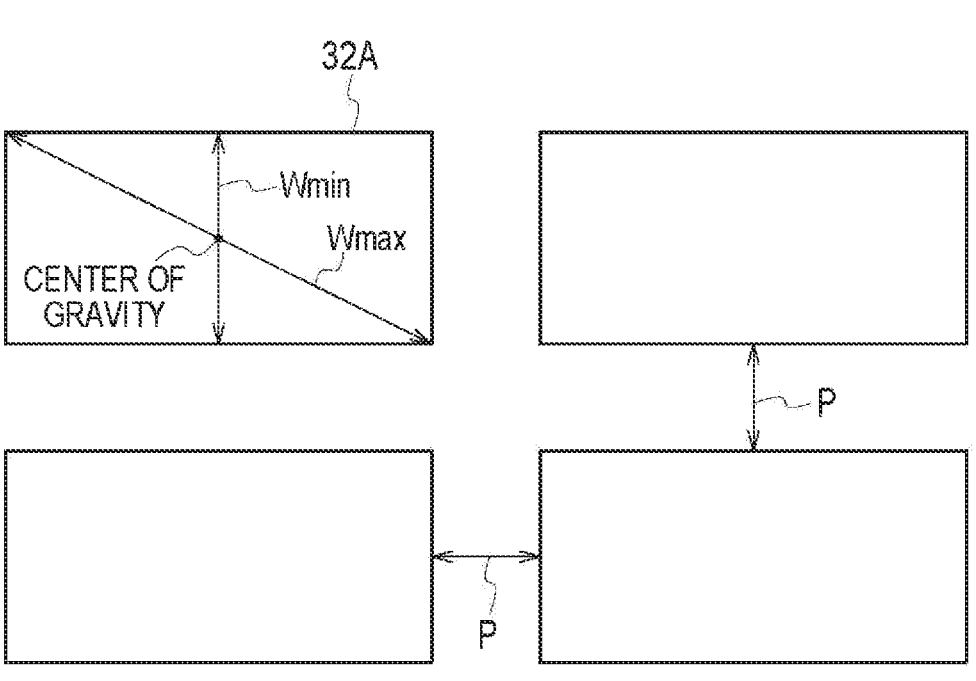
FIG. 9 is a diagram illustrating one example of a shape of an opening 32A according to the embodiment.
Figure 10:
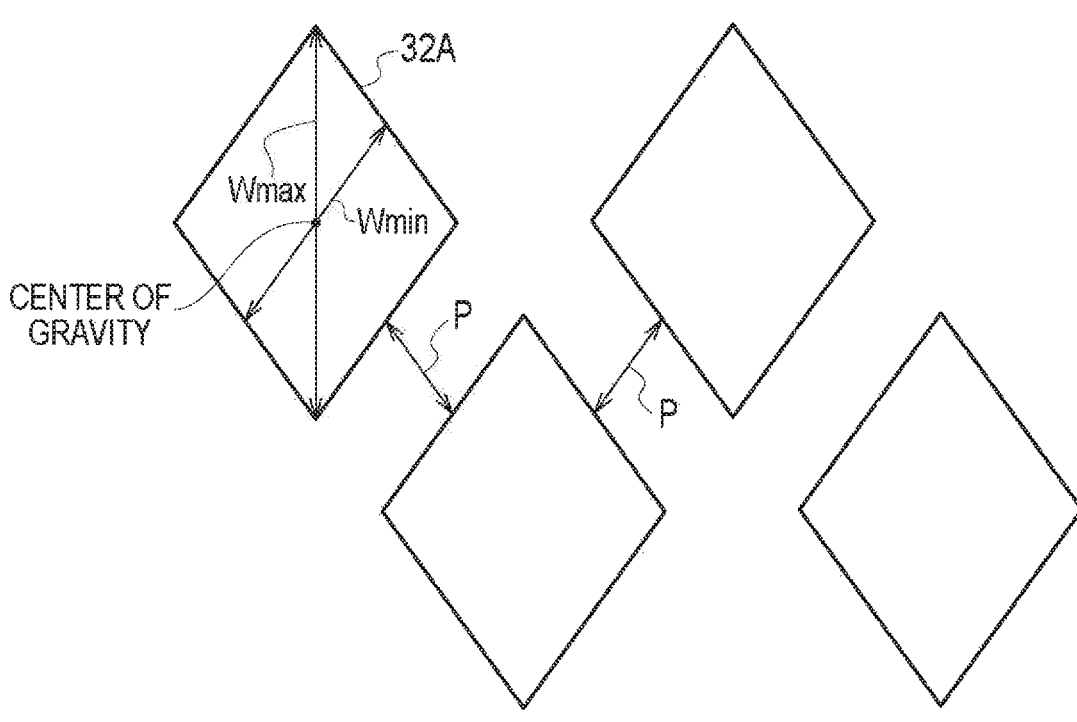
FIG. 10 is a diagram illustrating one example of the shape of the opening 32A according to the embodiment.
Figures 11, 12:
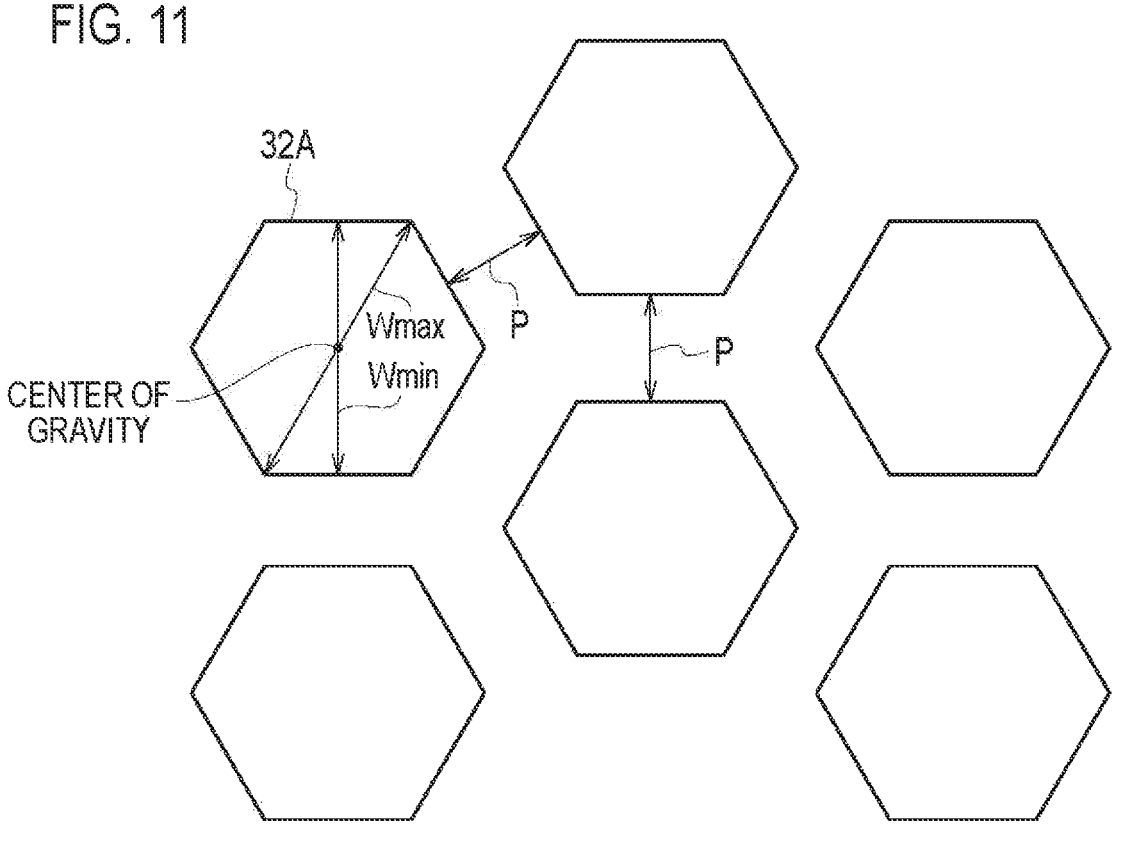
FIG. 11 is a diagram illustrating one example of the shape of the opening 32A according to the embodiment.
FIG. 12 is a diagram illustrating one example of the shape of the opening 32A according to the embodiment.

Here, as illustrated in FIG. 9 to FIG. 12, preferably each of the plurality of openings 32A has a shape selected from square, rectangular, diamond, hexagonal, and octagonal. As illustrated in FIG. 9 to FIG. 11, the shape of each of the plurality of openings 32A may be one type, and as illustrated in FIG. 12, may be two types. The shape of each of the plurality of openings 32A may be three types or more. Note that, from the perspective of arrangement efficiency, manufacturability, or the like of the plurality of openings 32A, preferably each of the plurality of openings 32A has a rectangular shape.

In the examples illustrated in FIG. 9 to FIG. 12, preferably the plurality of openings 32A are provided such that sides of the openings 32A adjacent to each other become parallel. Preferably an interval P of the openings 32A adjacent to each other is from 0.15 to 0.30 mm. In such a case, preferably the thickness of the mesh body 32 is from 0.1 to 1 mm.

The filter 33 is configured by a predetermined fiber and has a roughness to a degree such that the raw material pieces do not pass through. The filter 33 is provided on the downstream than the flavor source 31A. For example, the filter 33 is an acetate filter. The cap 34 is provided on the downstream (on the mouthpiece side) than the filter 33.

Note that, preferably the flavor source container 31 (here, containing the mesh body 32), the filter 33, and the cap 34 are adhered or welded to each other.

In the embodiment, preferably all openings provided in the mesh body 32 are the opening 32A described above, but the embodiment is not limited to this. The openings provided in the mesh body 32 may include openings other than the opening 32A described above.

(Connection State)

Figure 13:
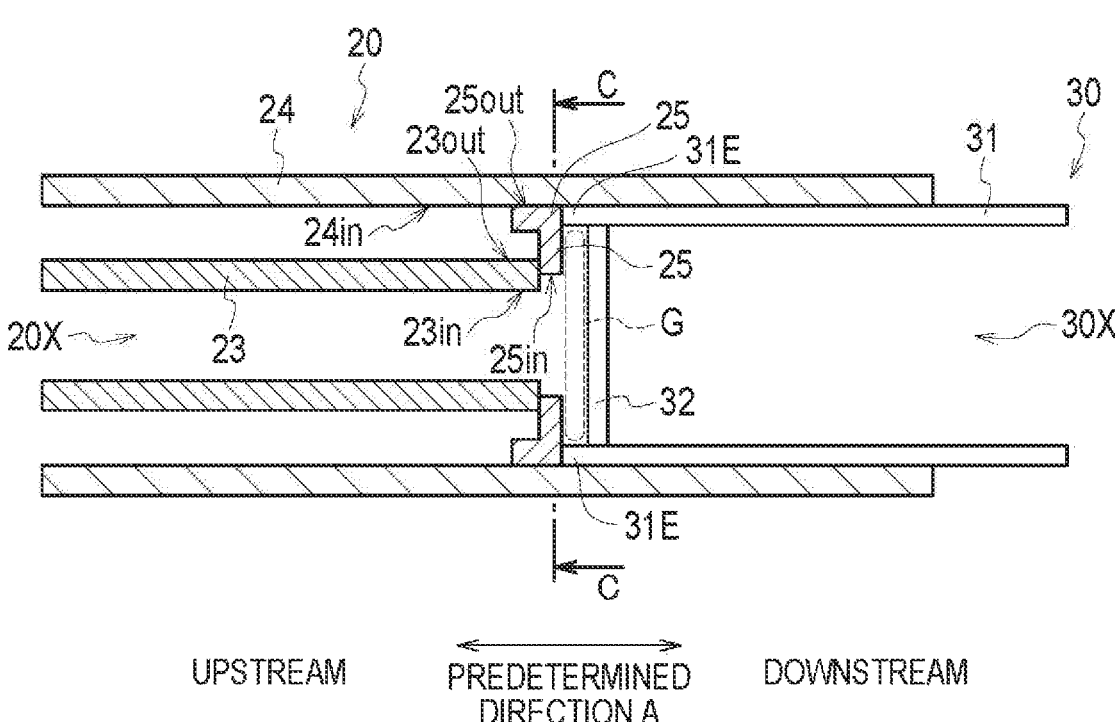
FIG. 13 is a diagram illustrating a connection state of the first cartridge 20 and the second cartridge 30 according to the embodiment.
Figure 14:
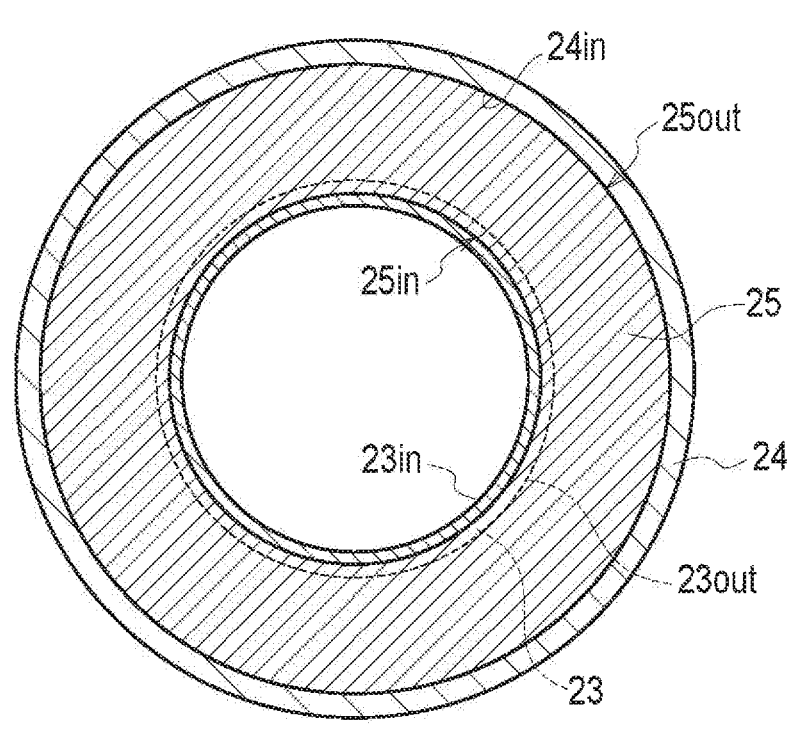
FIG. 14 is a diagram illustrating the cross-section taken along C-C illustrated in FIG. 13.

Hereinafter, a connection state of the first cartridge 20 and the second cartridge 30 according to the embodiment will be described. FIG. 13 is a diagram illustrating a connection state of the first cartridge 20 and the second cartridge 30 according to the embodiment. FIG. 14 is a diagram illustrating the cross-section taken along C-C illustrated in FIG. 13. However, it should be noted that in FIG. 13, the reservoir 21, the atomizer 22, the flavor source 31A, the filter 33, and the cap 34 are omitted.

As illustrated in FIG. 13, an aerosol flow adjustment chamber G that adjusts the flow of aerosol supplied from the first flow path 20X is provided between the first flow path 20X and the second flow path 30X such that polarization of the flow of the aerosol in the second flow path 30X is suppressed. In the embodiment, the aerosol flow adjustment chamber G is formed between the downstream end portion of the flow path forming body 23 and the upstream end portion of the flavor source container 31. More particularly, the aerosol flow adjustment chamber G is formed between the end cap 25 and the mesh body 32.

Here, a filling rate of the flavor source 31A accommodated in the flavor source container 31 may not be 100% of the capacity of the flavor source container 31. That is, a gap may be formed in the flavor source container 31. However, it is needless to say that the aerosol flow adjustment chamber G has a different gap generated by the filling rate of the flavor source 31A not being 100%.

In the embodiment, in a cross section orthogonal to the predetermined direction A, a shifted distance may be defined by a distance from an outer edge of the first flow path 20X to an outer surface of the second flow path 30X on a line from the center of gravity of the first flow path 20X toward the outside of the first flow path 20X. A length LG of the aerosol flow adjustment chamber G in the predetermined direction A may be determined based on the largest shift distance among the shift distances. That is, the length LG of the aerosol flow adjustment chamber G may be determined according to the largest shift distance. From the perspective of suppressing polarization of flow of the aerosol that flows inside the flavor source container 31, preferably the longer the largest shift distance, the longer the length LG of the aerosol flow adjustment chamber G. Preferably the length LG of the aerosol flow adjustment chamber G is ¹⁄₁₀ or more of the largest shift distance.

For example, as illustrated in FIG. 14, in the cross section orthogonal to the predetermined direction A, when the first flow path 20X and the second flow path 30X are coaxial circles, the length LG of the aerosol flow adjustment chamber G in the predetermined direction A is determined according to a difference (that is, the shift distance) between a radius R1 of the first flow path 20X and a radius R2 of the second flow path 30X.

In the embodiment, as described above, the flavor source container 31 has a protruding portion 31E that protrudes to the upstream side (in the embodiment, the flow path forming body 23 or the end cap 25 side) from an outer edge of an upstream end portion (here, the mesh body 32) of the flavor source container 31 in a cross section orthogonal to the aerosol flow path (predetermined direction A). That is, the flavor source container 31 has the protruding portion 31E (first protruding portion) as a spacer that forms the aerosol flow adjustment chamber G.

In the embodiment, preferably the entirety of the downstream end portion of the flow path forming body 23 (first flow path 20X) is exposed to the aerosol flow adjustment chamber G. Preferably the entirety of the upstream end portion of the flavor source container 31 (second flow path 30X) is exposed to the aerosol flow adjustment chamber G. Thereby, it is possible to effectively adjust the flow of the aerosol led from the first flow path 20X to the second flow path 30X using the aerosol flow adjustment chamber G.

Preferably the aerosol flow adjustment chamber G does not contain a part that protrudes more to the upstream side than the downstream end portion of the flow path forming body 23 (first flow path 20X). Preferably the aerosol flow adjustment chamber G does not contain a part that protrudes more to the downstream side than the upstream end portion of the flavor source container 31 (second flow path 30X). Thereby, it is possible to suppress retention of aerosol in an unnecessary gap.

Preferably an inner wall surface that constitutes the aerosol flow adjustment chamber G is continuous without including a step from the outer edge of the downstream end portion of the flow path forming body 23 (first flow path 20X) across the outer edge of the upstream end portion of the flavor source container 31 (second flow path 30X).

In the embodiment, as illustrated in FIG. 13 and FIG. 14, in the cross section orthogonal to the aerosol flow path (predetermined direction A), preferably an outer edge 25out of the end cap 25 contacts an inner wall surface 24in of the outer frame 24 and an inner edge 25in of the end cap 25 is positioned between the outer edge 25out of the flow path forming body 23 and the inner edge 25in of the flow path forming body 23. Thereby, it is difficult to remove the end cap 25 from the downstream side. In addition, when the end cap 25 is provided inside the outer frame 24, it is difficult for the end cap 25 to interfere with the flow path forming body 23.

(Control Circuit)

Figure 15:
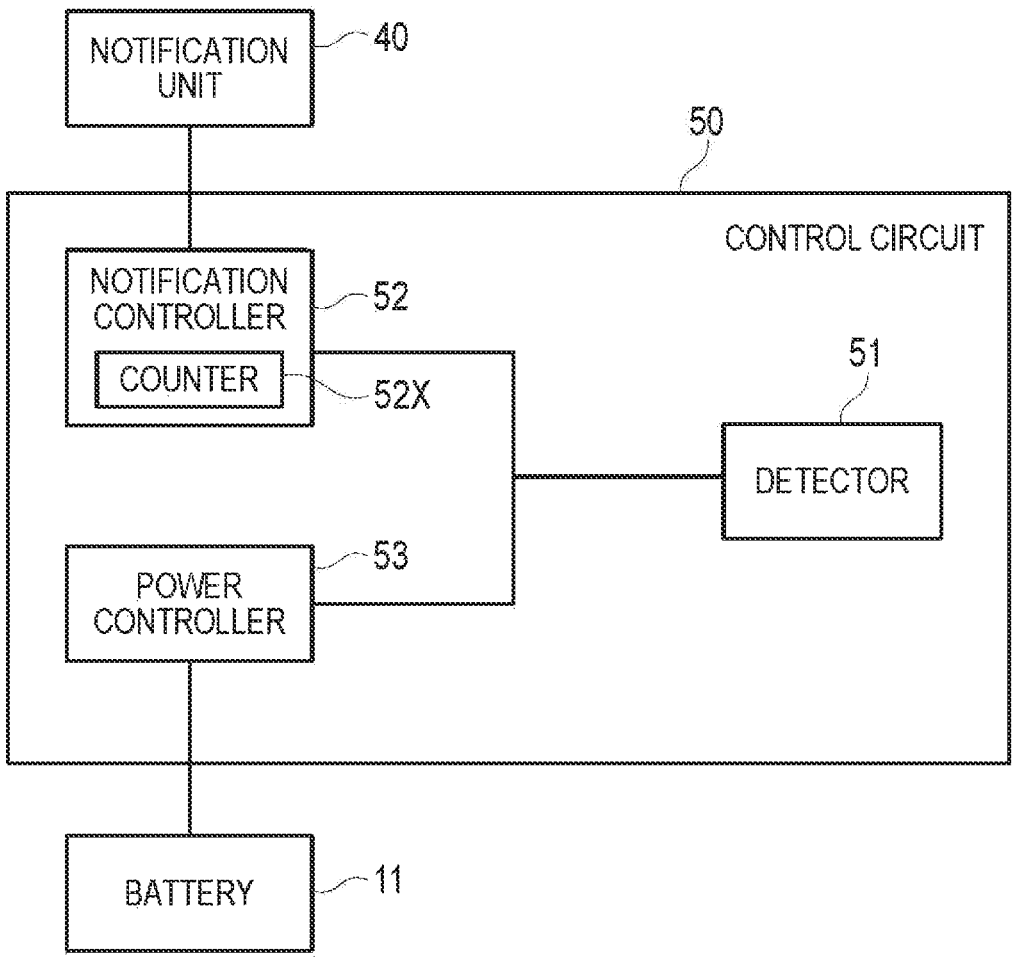
FIG. 15 is a diagram mainly illustrating a function block of a control circuit 50 according to the embodiment.

A control circuit according to the embodiment will be mainly described below. FIG. 15 is a diagram mainly illustrating a function block of a control circuit 50 according to an embodiment.

As illustrated in FIG. 15, the non-burning type flavor inhaler 1 has a notification unit 40 and the control circuit 50.

The notification unit 40 notifies a variety of information. The notification unit 40 may be constituted by a light emitting element, may be constituted by a vibration element, and may be constituted by a sound output element. The notification unit 40 may combine two or more elements out of the light emitting element, the vibration element, and the sound output element. Preferably the notification unit 40 is provided in the power source unit 10, but the embodiment is not limited thereto. The notification unit 40 may be provided in the first cartridge 20 and may be provided in the second cartridge 30.

The control circuit 50 has a detector 51, a notification controller 52, and a power controller 53.

The detector 51 detects the puff action. In such a case, the detector 51 is connected to an inhalation sensor and detects the puff action based on an output result of the inhalation sensor. In addition, the detector 51 detects power supply from the battery 11 to the atomizer 22. In such a case, the detector 51 is connected to a voltage sensor provided on a power line that connects the battery 11 and the atomizer 22 and detects power supply based on the output result of the voltage sensor.

The notification controller 52 controls the notification unit 40 to notify various information. For example, the notification controller 52 controls the notification unit 40 to notify a replacement timing of the second cartridge 30 according to detection of the replacement timing of the second cartridge 30. As described above, the notification unit 40 may notify the replacement timing of the second cartridge 30 due to light emission by the light emitting element, may notify the replacement timing of the second cartridge 30 due to vibration by the vibration element, and may notify the replacement timing of the second cartridge 30 due to sound output by the sound output element.

Here, the notification controller 52 detects the replacement timing of the second cartridge 30 based on the number of puff actions or an energization time of the atomizer 22. Note that, the number of puff actions may be set according to the puff action detected by the detector 51 described above. In the same manner, the energization time of the atomizer 22 may be set according to the power supply detected by the detector 51 described above.

Specifically, the notification controller 52 has a counter 52X that counts the number of puff actions or the energization time of the atomizer 22. When a count value of the counter 52X reaches a predetermined value, the notification controller 52 detects the replacement timing of the second cartridge 30 and resets the count value of the counter 52X. Note that, preferably the notification controller 52 resets the count value of the counter 52X after the second cartridge 30 is replaced. Alternatively, when the count value of the counter 52X reaches the predetermined value, the notification controller 52 notifies the replacement timing of the second cartridge 30 and resets the count value of the counter 52X according to the predetermined operation of the user. when a hardware interface (for example, a switch or button) for switching the power source of the non-burning type flavor inhaler 1 on or off or a hardware interface (for example, a switch or a button) for controlling power supply to the atomizer 22 is provided in the non-burning type flavor inhaler 1, the predetermined operation of the user may be an operation of the hardware interface. Alternatively, the predetermined user operation may be an operation of taking in breath from the mouthpiece of the non-burning type flavor inhaler 1 if it is possible for the detector 51 to detect the puff action. Alternatively, the predetermined operation of the user may be an operation of inhaling breath (for example, an operation of inhaling two times in a short time) in a mode in which it is possible for the detector 51 to detect the puff action and it is possible to identify a general puff action. The counter 52X may be a count type counter and may be a countdown type counter.

In the embodiment, preferably the notification controller 52 controls the notification unit 40 to notify the replacement timing of the first cartridge 20 according to detection of the replacement timing of the first cartridge 20. In such a case, preferably the notification controller 52 detects the replacement timing of the first cartridge 20 based on the number of replacement times of the second cartridge 30. More particularly, the notification controller 52 detects the replacement timing of the first cartridge 20 when the number of replacement times of the second cartridge 30 reaches a predetermined number of times.

In the embodiment, preferably the notification controller 52 controls the notification unit 40 to notify the replacement timing of the battery 11 or the charging timing of the battery 11 according to detection of the replacement timing of the battery 11 or the charging timing of the battery 11. In such a case, preferably the notification controller 52 detects the replacement timing of the battery 11 or the charging timing of the battery 11 based on output voltage of the battery 11. More particularly, preferably the notification controller 52 detects the replacement timing or the charging timing of the battery 11 when the output voltage of the battery 11 is a predetermined threshold.

However, the embodiment is not limited thereto, but the notification controller 52 may detect the replacement timing of the battery 11 or the charging timing of the battery 11 based on the number of puff actions or the energization time of the atomizer 22. More particularly, the notification controller 52 may detect the replacement timing of the battery 11 or the charging timing of the battery 11 when the number of puff actions or the energization time of the atomizer 22 exceeds the predetermined threshold.

Note that, the notification unit 40 notifies the replacement timing of the first cartridge 20, the replacement timing of the battery 11, or the charging timing of the battery 11 according to the light emission of the light emitting element, the vibration of the vibration element, or the output sound of the sound output element in the same manner as the replacement timing of the second cartridge 30.

The power controller 53 outputs a predetermined instruction to the battery 11 as an instruction to the battery 11, the predetermined instruction instructing the battery 11 to make the aerosol amount, atomized by the atomizer 22, falls within the desired range. The output of the predetermined instruction may be performed one time in each puff action. In addition, it should be noted that the power controller 53 instructs output of power to the atomizer 22 to the battery 11 in the puff period in which the puff action is performed, but does not instruct output of power to the atomizer 22 to the battery 11 in the non-puff period in which the puff action is not performed. Note that, the puff period and the non-puff period may be set according to the puff action detected by the detector 51 described above.

Here, the power controller 53 controls the predetermined instruction such that the aerosol amount atomized by the atomizer 22 falls within the desired range. For example, the power controller 53 modifies the predetermined instruction accompanying a reduction of the accumulated amount in the battery 11. In addition, the power controller 53 stops power supply from the battery 11 to the atomizer 22 when the predetermined period elapses from the start of power supply to the atomizer 22. In other words, the power controller 53 stops power supply from the battery 11 to the atomizer 22 when the puff period exceeds the predetermined period even in the puff period in which the puff action is actually performed by the user.

In addition, the power controller 53 stops power supply from the battery 11 to the atomizer 22 when the puff action ends even prior to the predetermined period elapse from the start of the puff action. Thereby, since the aerosol is not generated in the period in which the puff action is not performed (non-puff period), it is possible to suppress a situation in which droplets are generated by retaining and condensing the aerosol in the aerosol flow path in the non-puff period and the aerosol generated by the puff action next to the non-puff period is trapped in the droplets, and suppress a concern of hindering supply of the aerosol amount in the desired range, deterioration of taste caused by the droplets, and the like.

Here, the predetermined period is shorter than the upper limit value of the standard puff period derived from statistics of the puff period of the user. Furthermore, preferably the predetermined period is shorter than an average value of the puff period derived from statistics of the puff period of the user. Of course, the average value of the puff period is shorter than the upper limit value of the standard puff period.

Since the predetermined period is determined to suppress variation of the puff period of the user, it is necessary for there to be a certain number or more of users whose puff period is longer than the predetermined period. From such a perspective, preferably the predetermined period is derived from statistics. Furthermore, since it is possible for the energization time of the atomizer 22 in most puff actions is fixed in the predetermined period by the predetermined period being shorter than the average value of the puff period derived from statistics, it is possible to suppress variation of the aerosol amount caused by variance of the puff period of the user.

For example, the predetermined period is from one to three seconds. By the predetermined period being one second or more, the energization time of the atomizer 22 is not too short compared to the puff period, and therefore discomfort imparted to the user is mitigated. Meanwhile, it is possible to set the puff action in which the energization time of the atomizer 22 is fixed to the predetermined period to a certain number or more by the predetermined period being three seconds or less.

Furthermore, the predetermined period may be from 1.5 to 2.5 seconds. Thereby, it is possible to mitigate discomfort imparted to the user, and increase the puff action in which the energization time of the atomizer 22 is fixed to the predetermined period.

In the embodiment, preferably the predetermined period is set in advance. In such a case, preferably the predetermined period is determined according to the standard puff period derived from statistics of puff periods of a plurality of users.

Note that, the standard puff period may be derived from statistics of puff periods of users, and is a period between the lower limit value of puff periods of a plurality of users and the upper limit value of puff periods of a plurality of users. The lower limit value and the upper limit value, for example, may be derived from the upper limit value and the lower limit value of a 95% confidence interval of the average value and may be derived as $m \pm n\sigma$ (here, m is the average value, $\sigma$ is standard deviation, and n is a positive real number) based on distribution of puff period data of the users.

In the embodiment, preferably the power controller 53 modifies (or corrects) the predetermined instruction such that the aerosol amount atomized by the atomizer 22 falls within the desired range accompanying the reduction of the accumulated amount in the battery 11. For example, when the amount of power supplied from the battery 11 to the atomizer 22 is controlled by pulse control, preferably the power controller 53 increases a duty ratio output to the battery 11 in one puff action accompanying the reduction of the accumulated amount in the battery 11 as a modification of the predetermined instruction.

Figure 16:
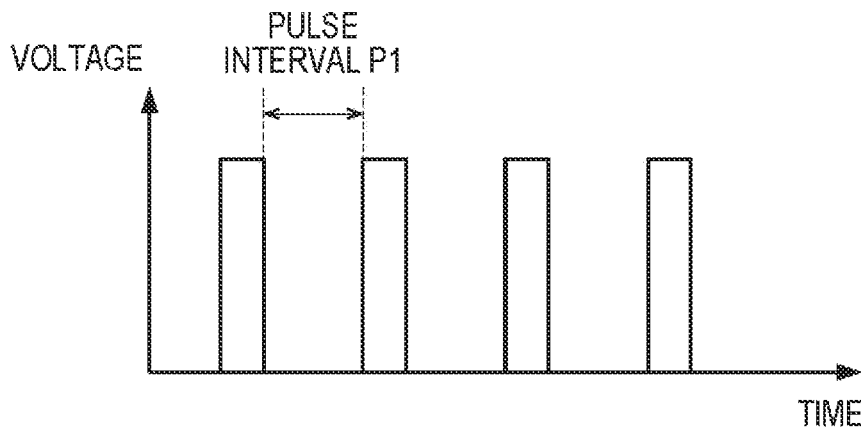
FIG. 16 is a diagram illustrating one example of duty ratio control according to the embodiment.
Figure 16:
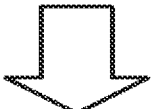
Figure 16:
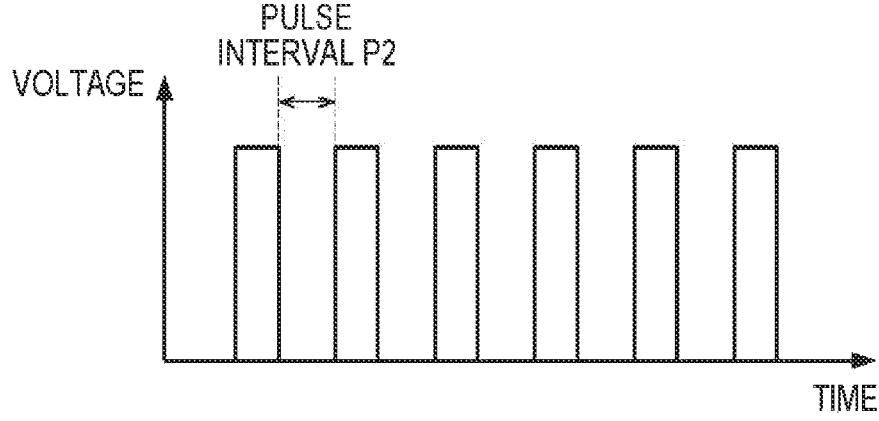

As illustrated in FIG. 16, for example, the power controller 53 controls an interval (pulse interval) of an on time at which power is supplied from the battery 11 to the atomizer 22. Specifically, the power controller 53 increases the duty ratio output to the battery 11 in one puff action by modifying a pulse interval P1 to a pulse interval P2.

Figure 17:
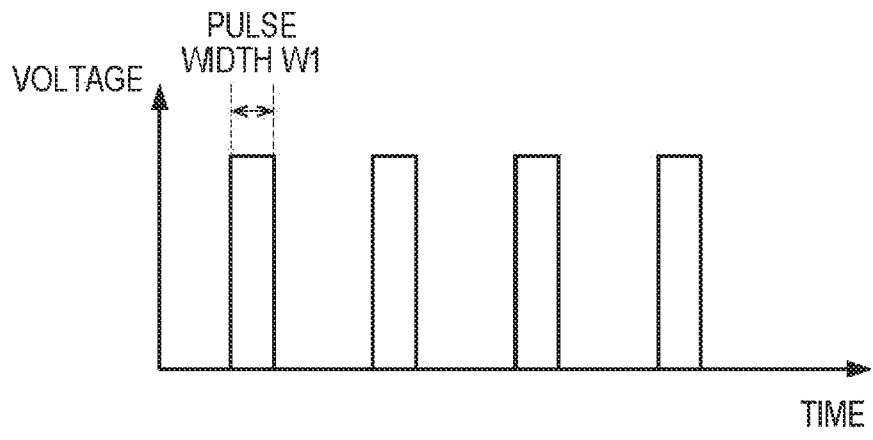
FIG. 17 is a diagram illustrating one example of duty ratio control according to the embodiment.
Figure 17:
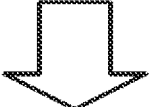
Figure 17:
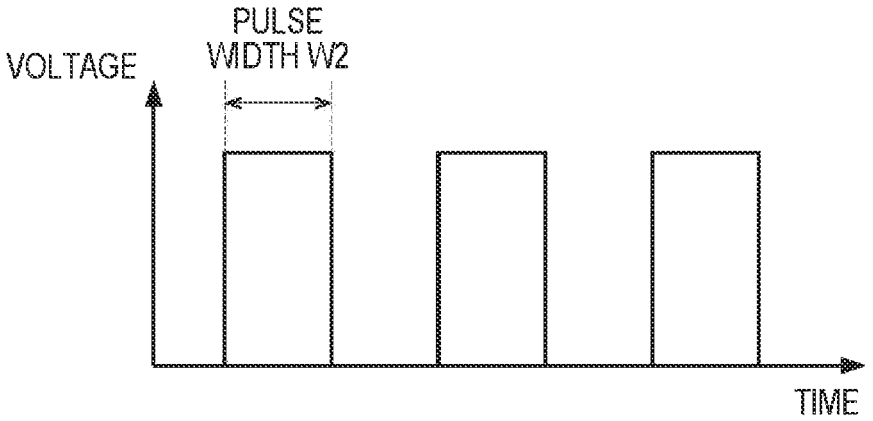

Alternatively, as illustrated in FIG. 17, the power controller 53 controls a length (pulse width) of the on time at which power is supplied from the battery 11 to the atomizer 22. Specifically, the power controller 53 increases the duty ratio output to the battery 11 in one puff action by modifying a pulse width W1 to a pulse width W2.

Note that, the power controller 53 may gradually increase the duty ratio and may continuously increase the duty ratio as a modification of the predetermined instruction accompanying the reduction of the accumulated amount in the battery 11.

In the embodiment, preferably the power controller 53 estimates the accumulated amount in the battery 11 based on a voltage value output from the battery 11. Alternatively, the power controller 53 may estimate the accumulated amount in the battery 11 based on the number of times of the puff action and the energization time of the atomizer 22. Note that, the number of puff actions may be set according to the puff action detected by the detector 51 described above. In the same manner, the energization time of the atomizer 22 may be set according to the power supply detected by the detector 51 described above.

In the embodiment, preferably the power controller 53 stops the power supply from the battery 11 to the atomizer 22 from the count value of the counter 52X reaching the predetermined value until the count value is reset. In other words, preferably the power controller 53 stops the power supply from the battery 11 to the atomizer 22 from the notification of the replacement timing of the second cartridge 30 until the count value is reset. That is, power supply from the battery 11 to the atomizer 22 is stopped until the second cartridge 30 is replaced. Accordingly, use of the second cartridge 30, in which it is only possible to impart a small amount of flavor to the aerosol, is suppressed.

(Control Method)

Figure 18:
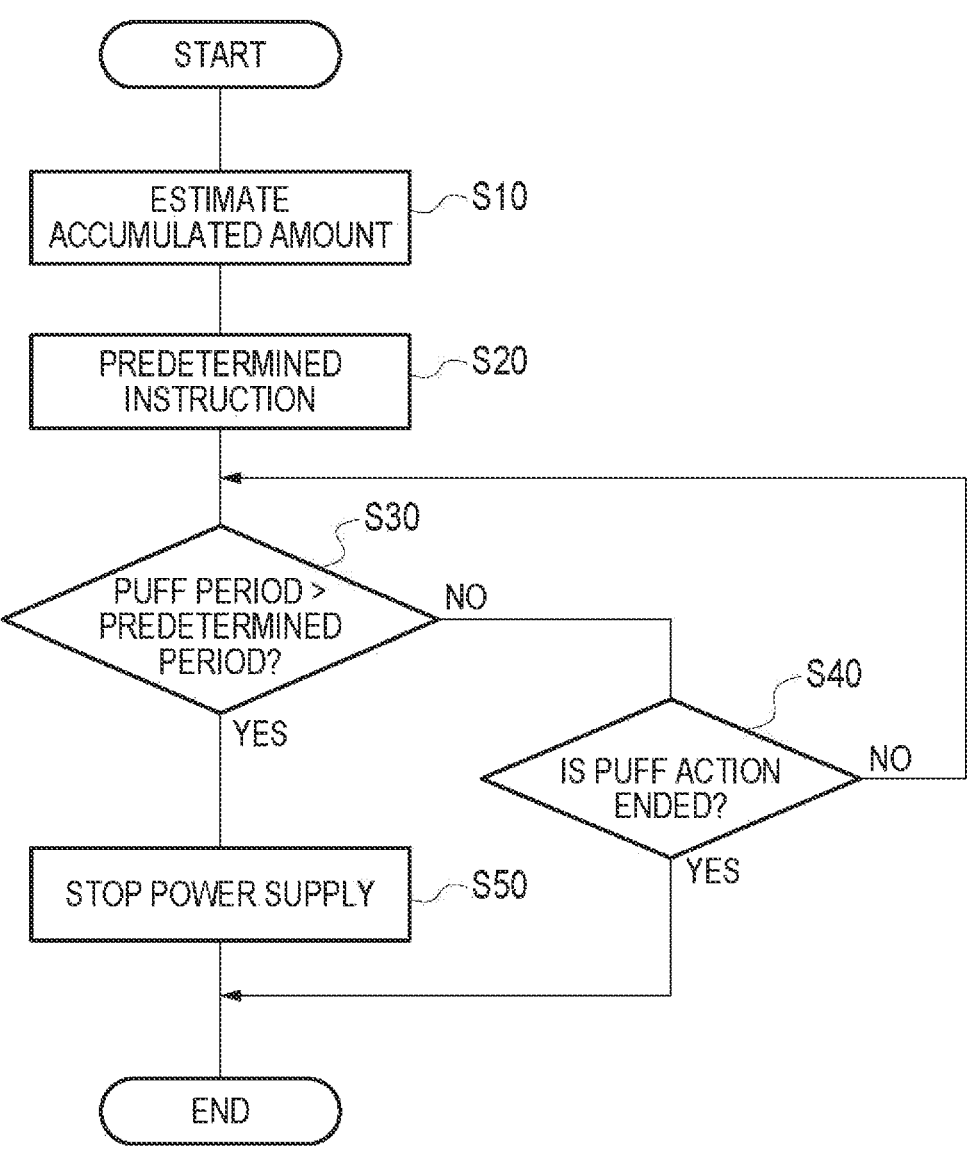
FIG. 18 is a flowchart illustrating a control method according to the embodiment.

A control method according to the embodiment will be described below. FIG. 18 is a flowchart illustrating the control method according to the embodiment. FIG. 18 is a flowchart illustrating the control method of the amount of power supplied from the battery 11 to the atomizer 22 in one puff action. It is noted that the flow illustrated in FIG. 18 starts in response to detection of the start of the puff action.

It is noted that as the premise of the flow illustrated in FIG. 18, the non-burning type flavor inhaler 1 (that is, the power controller 53) instructs to the battery 11 output of power to the atomizer 22 in the puff period in which the puff action is performed, but does not instruct to the battery 11 output of power to the atomizer 22 in the non-puff period in which the puff action is not performed.

As illustrated in FIG. 18, in step S10, the non-burning type flavor inhaler 1 (that is, the power controller 53) estimates the accumulated amount in the battery 11. As described above, preferably the non-burning type flavor inhaler 1 estimates the accumulated amount in the battery 11 based on the voltage value output from the battery 11.

In step S20, the non-burning type flavor inhaler 1 (that is, the power controller 53) determines the predetermined instruction (for example, the duty value) output to the battery 11. More particularly, the non-burning type flavor inhaler 1 determines the duty ratio output to the battery 11 such that the duty ratio increases along with the reduction of the accumulated amount in the battery 11. In other words, the non-burning type flavor inhaler 1 increases the duty ratio as a modification of the predetermined instruction.

In step S30, the non-burning type flavor inhaler 1 (that is, the power controller 53) determines whether or not the predetermined period elapses from the start of power supply to the atomizer 22. In other words, the non-burning type flavor inhaler 1 determines whether or not the puff period exceeds the predetermined period. When the determination result is YES, the non-burning type flavor inhaler 1 transitions to a process in step S50, and when the determination result is NO, the non-burning type flavor inhaler 1 transitions to a process in step S40.

In step S40, the non-burning type flavor inhaler 1 (that is, the power controller 53) estimates whether or not the puff action ends. When the determination result is NO, the non-burning type flavor inhaler 1 returns to the process in step S30, and when the determination result is YES, the non-burning type flavor inhaler 1 stops power supply to the atomizer 22 and ends the series of processes. Note that, as described above, the end of the puff action may be detected by the detector 51 if it is possible for the detector 51 to detect the puff action. Alternatively, the end of the puff action may be detected according to the operation of the hardware interface (for example, the switch or the button) for switching whether or not power is supplied to the atomizer 22.

In step S50, the non-burning type flavor inhaler 1 (that is, the power controller 53) stops power supply from the battery 11 to the atomizer 22 even in the puff period in which the puff action is actually performed by the user.

Operation and Effect

In the embodiment, the power controller 53 stops power supply from the battery 11 to the atomizer 22 when the predetermined period elapses from starting power supply to the atomizer 22. The predetermined period is shorter than the upper limit value of the standard puff period derived from statistics of puff periods of users. Accordingly, even if the non-burning type flavor inhaler is used by the user who has a puff period longer than the predetermined period, it is easy to suppress an extreme decrease of the accumulated amount in the battery 11 and easy to control the predetermined instruction such that the aerosol amount atomized by the atomizer 22 falls within the desired range.

In this manner, it is possible that the aerosol amount supplied per one puff action falls within the desired range through the puff action from the start of smoking (an initial stage in which an accumulated amount in a battery 11 is sufficient) until the end of smoking (that is, a final stage in which the accumulated amount in the battery 11 decreases), regardless of the length of a puff period of the user and the accumulated amount in the battery 11.

In the embodiment, the power controller 53 modifies the predetermined instruction output to the battery 11 in one puff action accompanying the reduction of the accumulated amount in the battery 11. It is possible to suppress a difference in the amount of power actually supplied from the battery 11 to the atomizer 22 between an initial step in which the accumulated amount in the battery 11 is sufficient and a final stage in which the accumulated amount in the battery 11 is insufficient. Thereby, it is possible for the aerosol amount atomized by the atomizer 22 to fall in the desired range regardless of the length of the puff period of the user and the accumulated amount in the battery 11.

In the embodiment, the notification controller 52 controls the notification unit 40 to notify a replacement timing of the second cartridge 30 according to detection of the replacement timing of the second cartridge 30. Accordingly, it is possible for the user to easily ascertain the replacement timing of the second cartridge 30.

In the embodiment, the notification controller 52 controls the notification unit 40 to notify the replacement timing of the first cartridge 20 according to detection of the replacement timing of the first cartridge 20. Accordingly, it is possible for the user to easily ascertain the replacement timing of the first cartridge 20.

In the embodiment, the notification controller 52 detects the replacement timing (lifespan) of the first cartridge 20 based on the number of replacement times of the second cartridge 30. Accordingly, detection of the replacement timing of the first cartridge 20 is easy. Furthermore, it is possible to mitigate a possibility that the lifespan of the first cartridge 20 comes to an end while the second cartridge 30 is in use. Note that, of course the replacement timing (lifespan) of the first cartridge 20 corresponds to the number (number of times of replacement) of the second cartridge 30 usable in one first cartridge 20.

In the embodiment, the notification controller 52 controls the notification unit 40 to notify the replacement timing of the battery 11 or the charging timing of the battery 11 according to detection of the replacement timing of the battery 11 or the charging timing of the battery 11. Accordingly, it is possible for the user to easily ascertain the replacement timing of the battery 11 or the charging timing of the battery 11.

In the embodiment, the power controller 53 stops the power supply from the battery 11 to the atomizer 22 from the count value of the counter 52X reaching the predetermined value until the count value is reset. Accordingly, power supply from the battery 11 to the atomizer 22 is stopped until the second cartridge 30 is replaced. Accordingly, use of the second cartridge 30, in which it is only possible to impart a small amount of flavor to the aerosol, is suppressed.

In the embodiment, the power controller 53 stops power supply from the battery 11 to the atomizer 22 when the predetermined instruction is controlled such that the aerosol amount atomized by the atomizer 22 falls within the desired range and a predetermined period elapses from the start of power supply to the atomizer 22. Accordingly, since the variation of the amount of power consumed in one puff action reduces, the detection accuracy of the replacement timing of the second cartridge 30 is improved when the replacement timing of the second cartridge 30 is detected based on the number of puff actions.

In the embodiment, an aerosol flow adjustment chamber G that adjusts the flow of aerosol supplied from the first flow path 20X is provided between the first flow path 20X and the second flow path 30X such that polarization of the flow of the aerosol in the second flow path 30X is suppressed. Thereby, the flavor source tends to pass through without the aerosol supplied from the first flow path 20X biasing in the second cartridge 30X.

In the embodiment, the reservoir 21 is positioned on the periphery of the flow path forming body 23 in a cross section orthogonal to the first flow path 20X (predetermined direction A). Thereby, it is possible to secure the volume of the reservoir 21 in which the aerosol source 21A is retained while suppressing the entire length of the first cartridge 20 in the first flow path 20X (predetermined direction A).

In the embodiment, in the cross section orthogonal to the aerosol flow path (predetermined direction A), the size of the second flow path 30X is larger than the size of the first flow path 20X. In other words, since the first flow path 20X is small in the cross section orthogonal to the aerosol flow path (predetermined direction A), it is possible to secure volume of the reservoir 21 positioned on the periphery of the flow path forming body 23. Since the size of the second flow path 30X is large in the cross section orthogonal to the aerosol flow path (predetermined direction A), it is possible to efficiently remove the flavor component from the flavor source 31A.

In the embodiment, in the cross section orthogonal to the aerosol flow path (predetermined direction A), the outer edge 25out of the end cap 25 contacts the inner wall surface 24in of the outer frame 24 and the inner edge 25in of the end cap 25 is positioned between the outer edge 25out of the flow path forming body 23 and the inner edge 25in of the flow path forming body 23. Thereby, it is difficult to remove the end cap 25 from the downstream side. In addition, when the end cap 25 is provided inside the outer frame 24, it is difficult for the end cap 25 to interfere with the flow path forming body 23.

In the embodiment, in a cross section orthogonal to the predetermined direction A, when a distance from an outer edge of the first flow path 20X to an outer surface of the second flow path 30X is a shifted distance on a line from the center of gravity of the first flow path 20X toward the outside of the first flow path 20X, a length LG of the aerosol flow adjustment chamber G in the predetermined direction A is determined according to the largest shift distance. Thereby, it is possible to appropriately adjust the flow of the aerosol led from the first 20X to the second flow path 30X using the aerosol flow adjustment chamber G, and the flavor source 31A tends to pass through without the aerosol supplied from the first flow path 20X biasing in the second cartridge 30.

In the embodiment, each of the plurality of openings 32A provided in the mesh body 32 has a polygon shape that has an internal angle of 180° or less. Each of the plurality of openings 32A has a minimum width Wmin having the smallest width and a maximum width Wmax having the largest width as widths through which each center of gravity of the plurality of openings 32A passes. Here, since the minimum width Wmin is smaller than the size of the raw material pieces included in the flavor source 31A, it is possible to suppress drop out of the raw material pieces included in the flavor source 31A, and since the maximum width Wmax is larger than the minimum width Wmin, it is possible to increase an opening ratio for the entirety of the mesh body.

In this manner, it is possible to secure the opening ratio for the entirety of the mesh body 32 while suppressing drop out of the raw material pieces forming the flavor source in the second cartridge 30 for the non-burning type flavor inhaler.

In the embodiment, the maximum width Wmax of the opening 32A is larger than the lower limit of the size of the raw material pieces included in the flavor source 31A. Accordingly, the opening ratio is improved for the entirety of the mesh body 32.

In the embodiment, the maximum width Wmax of the opening 32A is from $\sqrt{2}$ times to six times of the minimum width Wmin of the opening 32A. Accordingly, it is possible to improve the opening ratio for the entirety of the mesh body 32 by the maximum width Wmax being $\sqrt{2}$ times or more of the minimum width Wmin and maintain the strength of the mesh body 32 by the maximum width Wmax being six times or less of the minimum width Wmin.

In the embodiment, each of the plurality of openings 32A has a shape selected from square, rectangular, diamond, hexagonal, and octagonal. The plurality of openings 32A are provided such that sides of the openings 32A adjacent to each other become parallel. The interval P of the openings 32A that are adjacent to each other are from 0.15 to 0.30 mm. Thereby, it is possible to efficiently provide the plurality of openings 32A, and it is possible to maintain the strength of the mesh body 32 while improving the opening ratio for the entirety of the mesh body 32.

In the embodiment, the inner wall surface of the flavor source container 31 is provided with the rib 31R extending along the predetermined direction A from the upstream to the downstream. Accordingly, the flavor component tends to be removed from the flavor source 31A without the flow of the aerosol in the predetermined direction A being inhibited by the rib 31R in the flavor source container 31 while the rib 31R reinforces the flavor source container 31.

In the embodiment, the outer wall surface of the flavor source container 31 includes the taper part 31T that becomes wide from the upstream to the downstream. Accordingly, the second cartridge 30 tends to fit in the outer frame 24 of the first cartridge 20, and drop out of the second cartridge 30 is suppressed while permitting manufacturing error of the outline of the flavor source container 31.

In the embodiment, in the predetermined direction A, a length L2 from the mesh body 32 to the downstream end portion of the rib 31R is shorter than a length L1 from the mesh body 32 to the downstream end portion of the flavor source container 31. In other words, the downstream end portion of the rib 31R comes into contact with the filter 33 without reaching the downstream end portion of the flavor source container 31. Accordingly, a function of positioning the filter 33 can be achieved while reinforcing the flavor source container 31 using the rib 31R.

First Modification

A first modification of the embodiment will be described below. Differences from the embodiment are mainly described below.

Specifically, in the embodiment, the flavor source container 31 has the protruding portion 31E (first protruding portion) as a spacer that forms the aerosol flow adjustment chamber G. Conversely, in the first modification, the flavor source container 31 does not have the protruding portion 31E.

Figure 19:
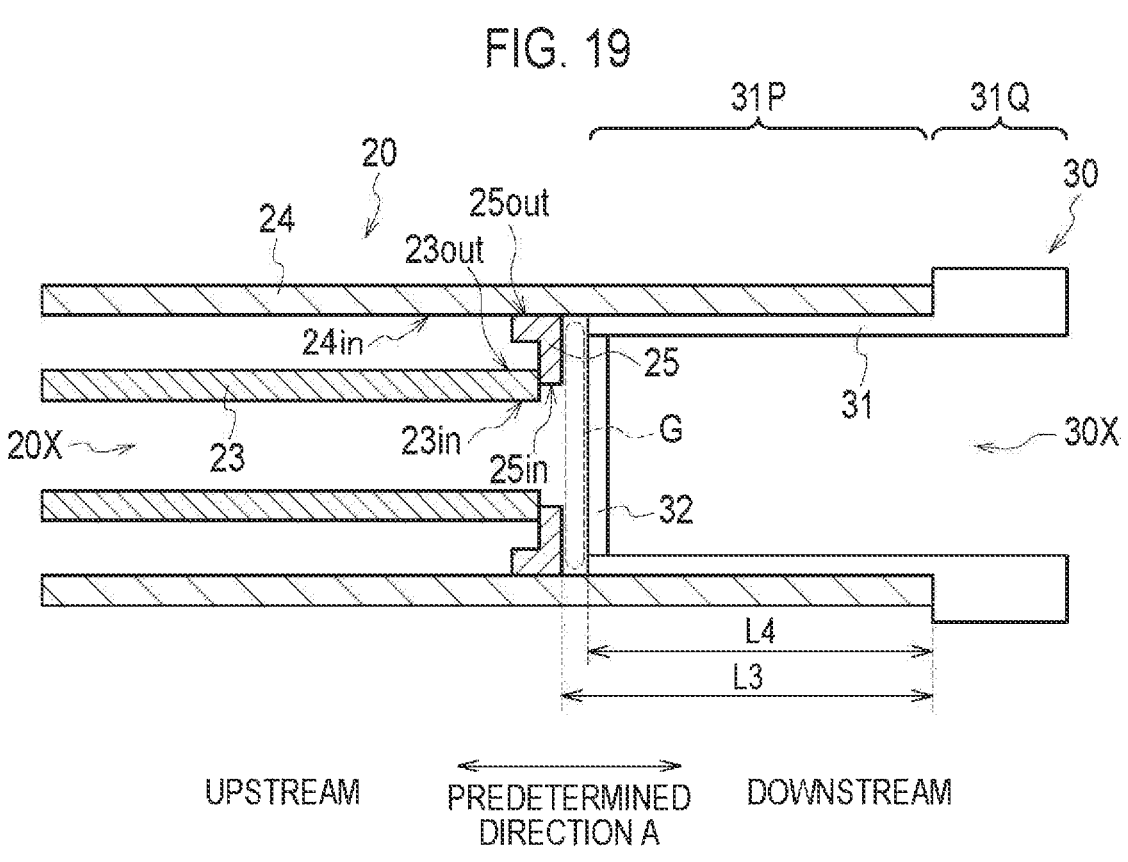
FIG. 19 is a diagram illustrating a connection state of the first cartridge 20 and the second cartridge 30 according to a first modification.

FIG. 19 is a diagram illustrating a connection state of the first cartridge 20 and the second cartridge 30 according to the first modification. However, it should be noted that in FIG. 19, the reservoir 21, the atomizer 22, the flavor source 31A, the filter 33, and the cap 34 are omitted.

As illustrated in FIG. 19, the flavor source container 31 has a main body portion 31P that accommodates the flavor source 31A and a flange portion 31Q provided on the side surface of the main body portion 31P. It should be noted that in the cross section orthogonal to the aerosol flow path (predetermined direction A), the flange portion 31Q overhangs to the outside than the main body portion 31P, and overhangs outside to the same degree or more as the inner surface of the outer frame 24. In FIG. 19, the flange portion 31Q is provided on the side surface of the downstream end portion of the main body portion 31P, but is not limited thereto, and may be provided somewhere on the side surface of the main body portion 31P in a mode of being locked to the inner surface of the outer frame 24.

Here, a distance L3 from the downstream end portion of the outer frame 24 to the end cap 25 (that is, a distance from a part in which the outer frame 24 abuts the flange portion 31Q to the downstream end portion of the end cap 25) is longer than a length L4 of the main body portion 31P (that is, a distance from an upstream end portion of the flange portion 31Q to the upstream end portion of the main body portion 31P). Accordingly, the aerosol flow adjustment chamber G that adjusts the flow of aerosol supplied from first flow path 20X is formed even if the flavor source container 31 does not have the protruding portion 31E by the flange portion 31Q catching on the downstream end portion of the outer frame 24.

Note that, when the first cartridge 20 does not have the end cap 25, a distance from the downstream end portion of the outer frame 24 to the downstream end portion of the flow path forming body 23 (that is, a distance from a part in which the outer frame 24 abuts the flange portion 31Q to the downstream end portion of the flow path forming body 23) is longer than a length of the main body portion 31P (that is, a distance from an upstream end portion of the flange portion 31Q to the upstream end portion of the main body portion 31P).

Second Modification

A second modification of the embodiment will be described below. Differences from the embodiment are mainly described below.

Specifically, in the embodiment, the flavor source container 31 has the protruding portion 31E (first protruding portion) as a spacer that forms the aerosol flow adjustment chamber G. Conversely, in the second modification, the flavor source container 31 does not have the protruding portion 31E.

Figure 20:
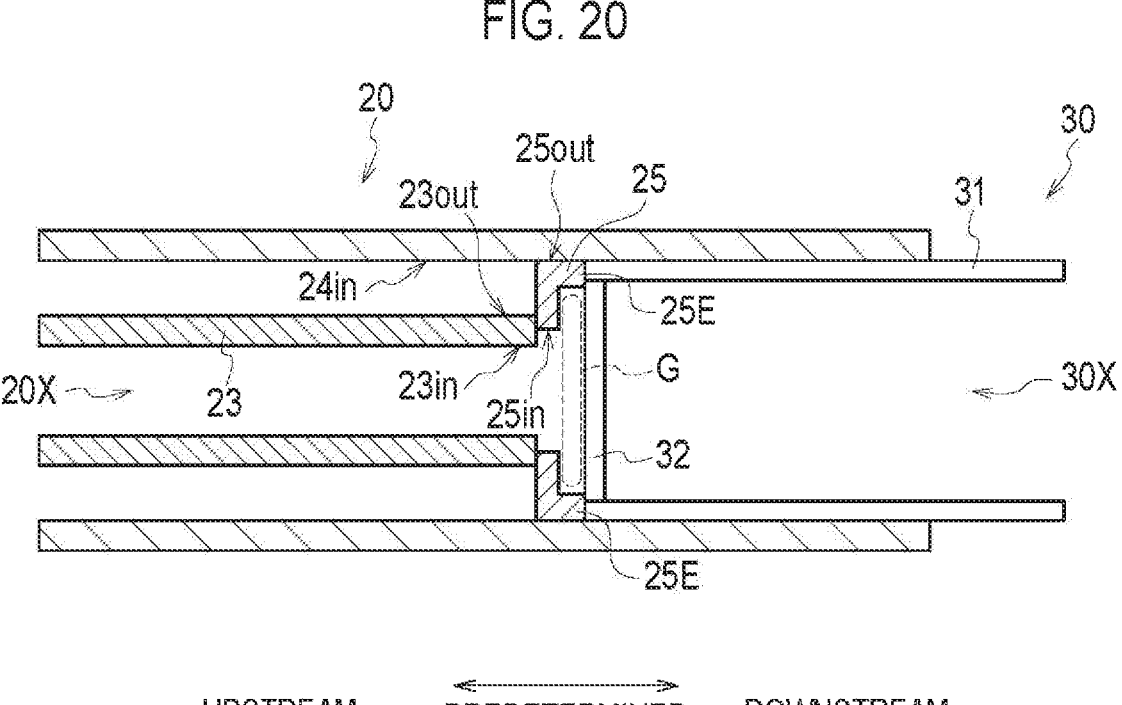
FIG. 20 is a diagram illustrating a connection state of the first cartridge 20 and the second cartridge 30 according to a second modification.

FIG. 20 is a diagram illustrating a connection state of the first cartridge 20 and the second cartridge 30 according to the second modification. However, it should be noted that in FIG. 20, the reservoir 21, the atomizer 22, the flavor source 31A, the filter 33, and the cap 34 are omitted. The protruding portion 25E contacts the upstream end portion of the flavor source container 31 (preferably, the outer edge of the upstream end portion).

As illustrated in FIG. 20, the end cap 25 has the protruding portion 25E that protrudes from the outer edge of the downstream end portion of the end cap 25 to the downstream side (flavor source container 31 side) in the cross section orthogonal to the aerosol flow path (predetermined direction A). The protruding portion 25E may be continuously provided along the outer edge of the end cap 25 and may be intermittently provided along the outer edge of the end cap 25. Note that, when there is a gap between the outer frame 24 and the flavor source container 31, preferably the protruding portion 25E is continuously provided along the outer edge of the end cap 25. Thereby, it is possible to suppress retention of aerosol in the gap formed in the upstream part of a taper part 31T.

In this manner, the aerosol flow adjustment chamber G that adjusts the flow of the aerosol supplied from first flow path 20X is formed even if the flavor source container 31 does not have the protruding portion 31E by the protruding portion 25E being provided in place of the protruding portion 31E.

Note that, when the first cartridge 20 does not have the end cap 25, the flow path forming body 23 has the same protruding portion as the protruding portion 25E that protrudes from the outer edge of the downstream end portion of the flow path forming body 23 to the downstream side (flavor source container 31 side) in the cross section orthogonal to the aerosol flow path (predetermined direction A).

Third Modification

A third modification of the embodiment will be described below. Differences from the embodiment are mainly described below.

Specifically, in the embodiment, the first flow path 20X completely overlaps the second flow path 30X viewed from the predetermined direction A. In addition, in the cross section orthogonal to the aerosol flow path (predetermined direction A), preferably the size of the second flow path 30X is larger than the size of the first flow path 20X.

Figure 21:
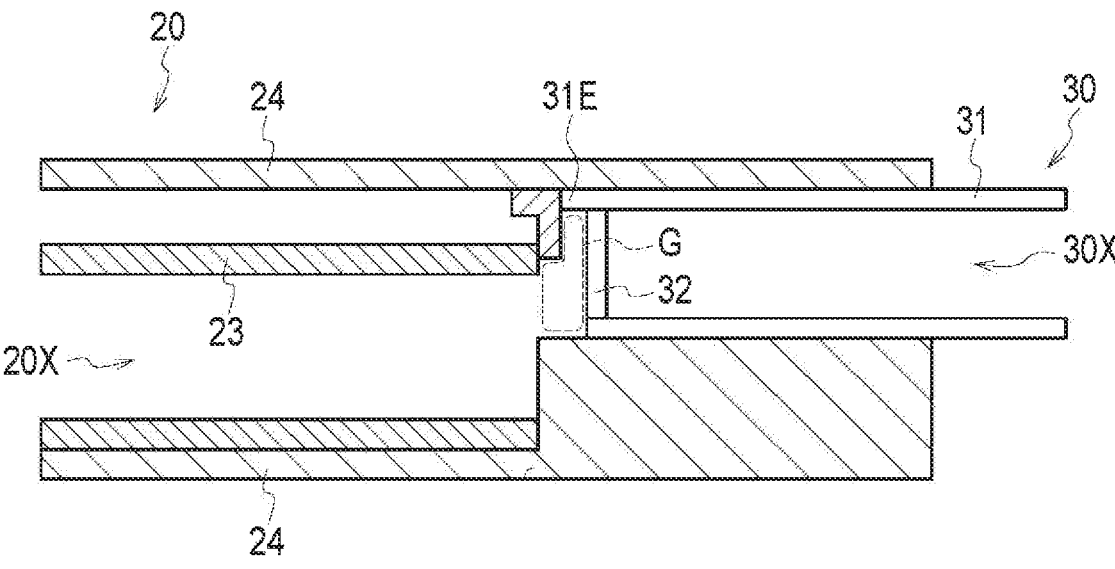
FIG. 21 is a diagram illustrating a connection state of the first cartridge 20 and the second cartridge 30 according to a third modification.

In contrast, in the third modification, as illustrated in FIG. 21, viewed from the predetermined direction A, the first flow path 20X is shifted from the second flow path 30X without completely overlapping the second flow path 30X. In such a case, in the cross section orthogonal to the aerosol flow path (predetermined direction A), the size of the second flow path 30X is not particularly limited, but may be to the same degree as the size of the first flow path 20X, and may be smaller than the size of the first flow path 20X. However, the size of the second flow path 30X may be larger than the size of the first flow path 20X.

Fourth Modification

Hereinafter, the fourth modification of the embodiment will be described with reference to FIG. 22 to FIG. 25. Differences from the embodiment are mainly described below. In FIG. 22 to FIG. 25, the vertical axis represents the aerosol amount (amount of total particulate matter (TPM)) (mg/puff action), and the horizontal axis represents the number of puff actions (puff number). The vertical axis and the horizontal axis represent larger values as it is away from the intersection point of both axes.

In the fourth modification, in the same manner as in the embodiment, the power controller 53 stops power supply from the battery 11 to the atomizer 22 when a predetermined period elapses from the start of power supply to the atomizer 22. The predetermined period is shorter than an upper limit value of a standard puff period derived from statistics of puff periods of users.

Note that, the aerosol amount atomized by the atomizer 22 depends on the puff period in which the puff action is actually performed by the user and the output voltage output to the battery 11. Here, the explanation may be given assuming that the standard puff period derived from statistics of the puff period of the user may be considered as following a normal distribution having an average of 2.4 seconds and a standard deviation of 1 second. Note that, in such a case, as described above, the upper limit value of the standard puff period is derived as $m+n\sigma$ (here, m is the average value, $\sigma$ is standard deviation, and n is a positive real number), and for example, is to the degree of three to four seconds. Here, description is made assuming a case in which the upper limit value of the standard puff period is three seconds (n=0.6).

Figure 22:
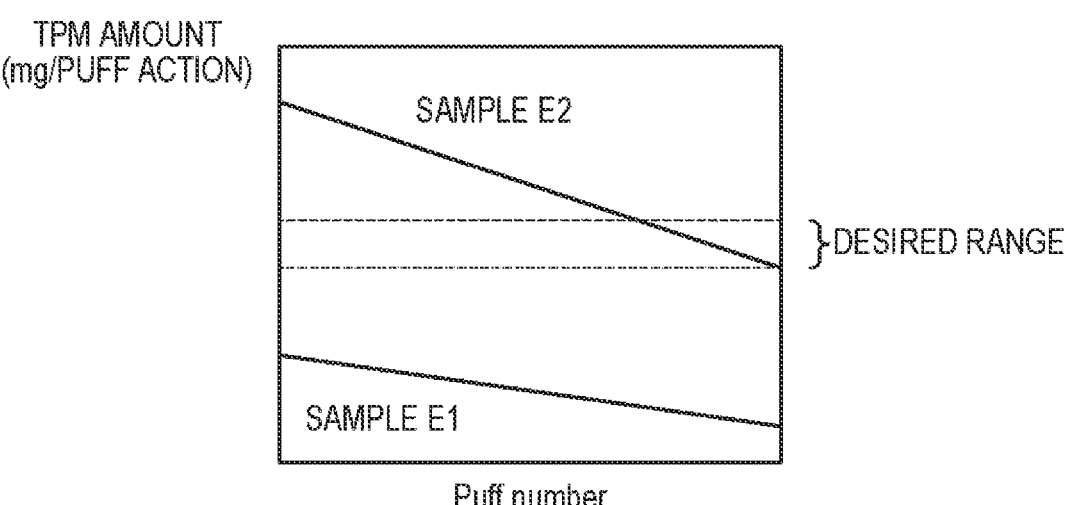
FIG. 22 is a diagram for explaining an aerosol amount according to a fourth modification.

In sample E, an initial value of the output voltage of the battery 11 is 4.2 V, and the battery capacity of the battery 11 is 220 mAh. In addition, the atomizer 22 is constituted by the heating wire wound around, and the resistance value of the heating wire is 3.5Ω. In FIG. 22, a sample E1 indicates a relationship between the number of puffs and the aerosol amount when sample E is inhaled in the puff period of two seconds per one puff action, and a sample E2 indicates the relationship between the number of puffs and the aerosol amount when sample E is inhaled in the puff period of three seconds per one puff action. Here, it should be noted that when the standard puff period follows an average of 2.4 seconds and normal distribution of the standard deviation of one second, probability of inhaling in the puff period of three seconds or more per one puff action as indicated in sample E2 is approximately 27%, and is a circumstance that sufficiently occurs.

Figure 23:
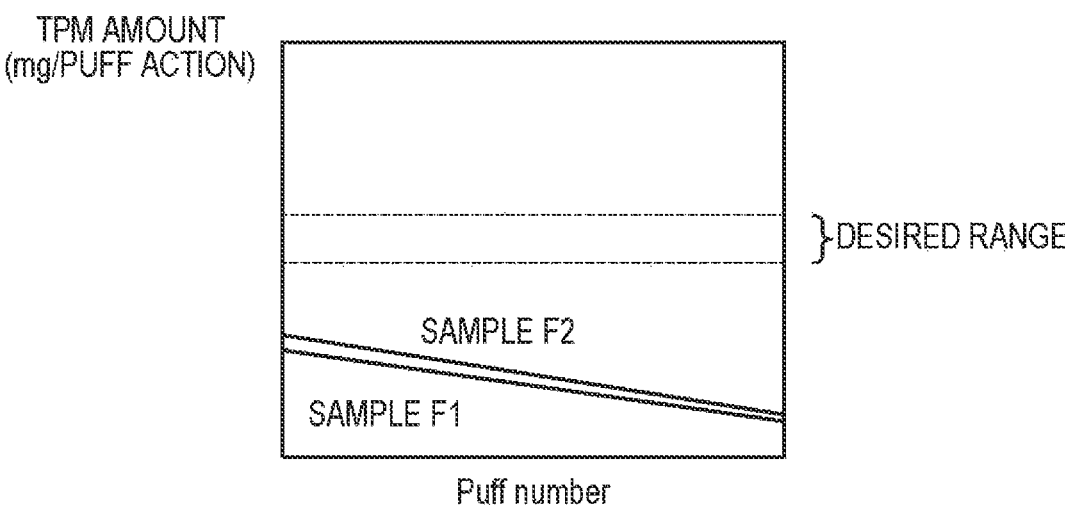
FIG. 23 is a diagram for explaining the aerosol amount according to the fourth modification.

In sample F, the configuration of the battery 11 and the atomizer 22 is the same as the sample E. In FIG. 23, a sample F1 indicates a relationship between the number of puffs and the aerosol amount when sample F is inhaled in the puff period of two seconds per one puff action, and a sample F2 indicates the relationship between the number of puffs and the aerosol amount when sample F is inhaled in the puff period of three seconds per one puff action. However, in the sample F1 and the sample F2, the power controller 53 stops power supply from the battery 11 to the atomizer 22 when a predetermined period elapse from the start of power supply to the atomizer 22 (here, 2.2 seconds). Here, it should be noted that the predetermined period is 2.2 seconds that is shorter than the upper limit value of the standard puff period derived from statistics of the puff period of the user, and is shorter than the average value of the puff period.

Figure 24:
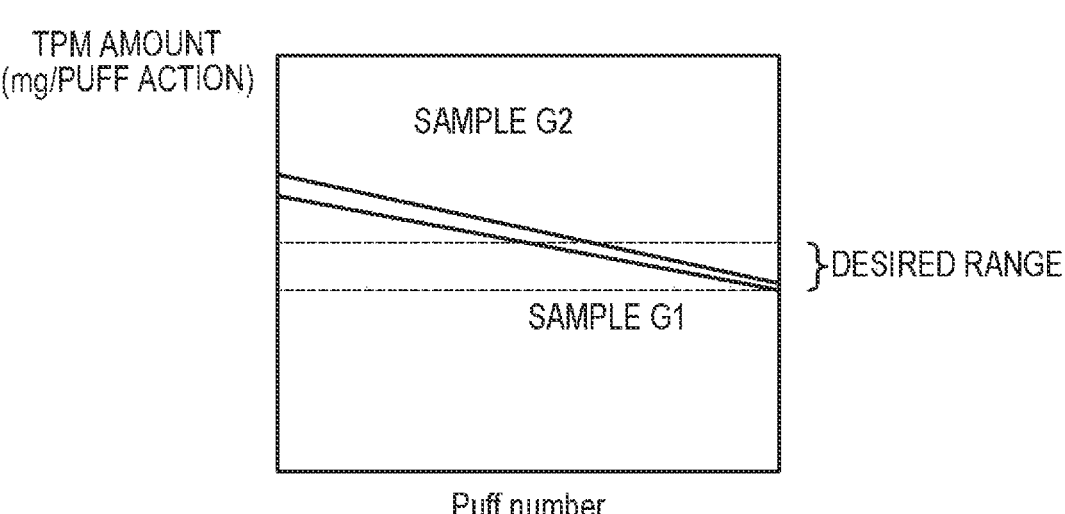
FIG. 24 is a diagram for explaining the aerosol amount according to the fourth modification.

In a sample G, the configuration of the battery 11 is the same as the samples E and F. Meanwhile, the atomizer 22 is constituted by the heating wire wound at a predetermined pitch, and is different from samples E and F in that the resistance value of the heating wire is 2.9Ω. In FIG. 24, a sample G1 indicates a relationship between the number of puffs and the aerosol amount when the sample G is inhaled in the puff period of two seconds per one puff action, and a sample G2 indicates the relationship between the number of puffs and the aerosol amount when the sample G is inhaled in the puff period of three seconds per one puff action. However, in the sample G1 and the sample G2, the power controller 53 stops power supply from the battery 11 to the atomizer 22 when a predetermined period elapse from the start of power supply to the atomizer 22 (here, 2.2 seconds).

Figure 25:
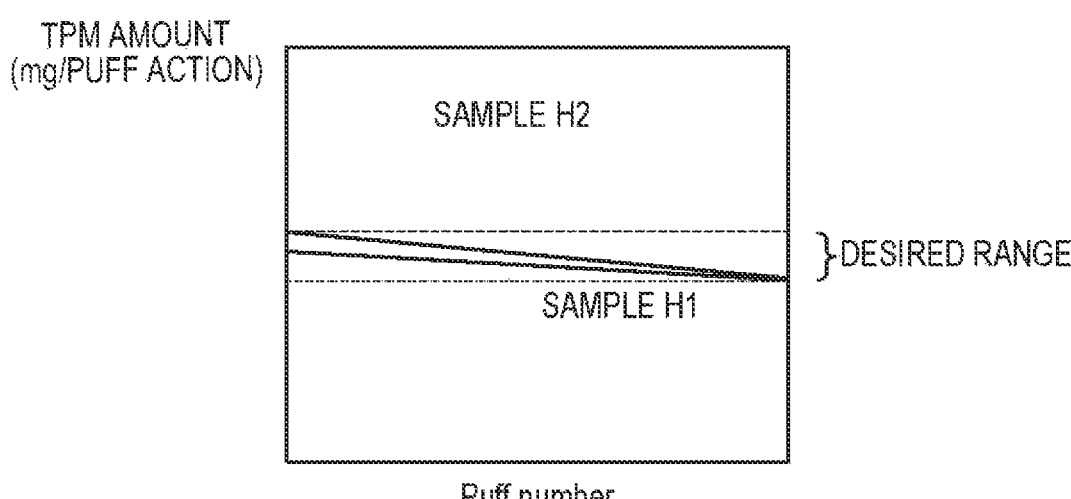
FIG. 25 is a diagram for explaining the aerosol amount according to the fourth modification.

In a sample H, the configuration of the battery 11 and the atomizer 22 is the same as the sample G. However, the predetermined pitch of the heating wire forming the atomizer 22 is uniformly wound in a range of from 0.35 to 0.40 mm, and is narrower than the predetermined pitch of the sample G. In FIG. 25, a sample H1 indicates a relationship between the number of puffs and the aerosol amount when the sample H is inhaled in the puff period of two seconds per one puff action, and a sample H2 indicates the relationship between the number of puffs and the aerosol amount when the sample H is inhaled in the puff period of three seconds per one puff action. In addition, in the sample H1 and the sample H2, in the same manner as the sample G, the power controller 53 stops power supply from the battery 11 to the atomizer 22 when a predetermined period elapse from the start of power supply to the atomizer 22 (here, 2.2 seconds). However, in the sample H1 and the sample H2, the duty ratio is modified during power supply to the atomizer 22 according to the value of the output voltage of the battery 11 detected by the detector 51. Specifically, as described above, since the output voltage of the battery 11 lowers accompanying reduction of the accumulated amount in the battery 11, the duty ratio of the power supplied to the atomizer 22 is increased according to lowering of the output voltage of the battery 11.

Under such premises, as illustrated in FIG. 22, the sample E in which the puff period and the energization time to the atomizer 22 match regardless of the length of the puff period is modified such that the aerosol amount is large when the puff period is three seconds and when the puff period is two seconds. In addition, as understood by comparing inclination of the sample E1 and the sample E2, variation of the aerosol amount from the initial puff up to the final puff is more remarkable the longer the puff period, that is, the energization time.

Focusing on such results, an inventor and the like found that when the predetermined period is set shorter than the upper limit value of the standard puff period derived from statistics of the puff period of the user and the predetermined period elapses from the start of power supply to the atomizer 22 in one puff action, as illustrated in FIG. 23, it is possible to suppress variation of the aerosol amount from the initial puff up to the final puff even in the sample F2 in which the puff period is three seconds by stopping power supply from the battery 11 to the atomizer 22. Thereby, it is possible to suppress variation of the aerosol amount because of variation of the puff period of the user.

Furthermore, focusing on such results, as illustrated in FIG. 24, the inventor and the like found that it is possible for the aerosol amount atomized by the atomizer 22 falls within the desired range across the number of longer puffs from the initial puff to the final puff by modifying the configuration of the atomizer 22 such that the aerosol amount atomized by the atomizer 22 falls within the desired range when the energization time of the atomizer 22 is the predetermined period. Here, comparing the sample G2 illustrated in FIG. 24 and the sample F2 illustrated in FIG. 23, in the sample G2, the aerosol amount atomized by the atomizer 22 falls within the desired range across the number of puffs that are longer than the sample F2, whereas a fluctuation range of the aerosol amount from the initial puff to the final puff is increased more than the fluctuation range in the sample F2. Thereby, the amount of power supply from the battery 11 to the atomizer 22 increases in one puff action by modifying the configuration of the atomizer 22.

Furthermore, focusing on such results, the inventor and the like found that it is possible to mitigate a reduction rate of the aerosol amount by carrying out the following modifications. Specifically, it is possible to mitigate the reduction rate of the aerosol amount by increasing the duty ratio of the power supplied to the atomizer 22 in response to lowering of the output voltage of the battery 11. In addition, it is possible to mitigate the reduction rate of the aerosol amount even if the predetermined pitch of the heating wire is narrow. As illustrated in FIG. 25, by such a modification, it was found that the aerosol amount atomized by the atomizer 22 falls within the desired range across the entire period from the initial puff to the final puff in either of H1 in which the puff period is two seconds and H2 in which the puff period is three seconds.

Based on these results, the inventor and the like newly found that it is effective to perform control as indicated below on the power supply from the battery 11 to the atomizer 22.

(1) The power controller 53 stops power supply from the battery 11 to the atomizer 22 when a predetermined period elapses from the start of power supply to the atomizer 22. Here, preferably the predetermined period is shorter than the upper limit value of the standard puff period derived from statistics of the puff period of the user, and is shorter than the average value of the puff period.

(2) The resistance value of the heating wire of the atomizer 22 is determined such that the aerosol amount in the desired range is atomized when the energization time of the atomizer 22 is the predetermined period. Here, preferably the resistance value of the heating wire is determined such that the voltage supplied from the battery 11 to the atomizer 22 is set as the voltage in the final stage in which the accumulated amount in the battery 11 is insufficient and the aerosol amount atomized by the atomizer 22 falls within the desired range when the energization time of the atomizer 22 is the predetermined period.

(3) Furthermore, the power controller 53 increases the duty ratio of power supplied to the atomizer 22 in response to a reduction of the output voltage of the battery 11 such that the aerosol amount atomized by the atomizer 22 falls within the desired range across the entire period from the initial puff to the final puff.

By the control described above, regardless of the length of the puff period of the user, it is possible to suppress a difference of the amount of power actually supplied from the battery 11 to the atomizer 22, through the initial step, in which the accumulated amount in the battery 11 is sufficient, to the final step, in which the accumulated amount in the battery 11 is insufficient, and it is easy for the aerosol amount to fall within the desired range.

That is, in the fourth modification, the atomizer 22 is configured to be capable of atomizing the aerosol of a larger amount than the desired range of the amount of supply of the aerosol in one puff action at the start of use of at least the atomizer 22 (in other words, while the battery 11 is fully charged) by adjusting the predetermined pitch of the heating wire forming the atomizer 22 and the resistance value.

Under such premises, the predetermined instruction (here, duty ratio) output from the power controller 53 is determined based on the length of the predetermined period such that the aerosol amount atomized by the atomizer 22 in the predetermined period falls within the desired range. In other words, the predetermined instruction is determined based on the length of the predetermined period in a state in which variance of the aerosol amount caused by the variance of the length of the puff period of the user is suppressed by determining the predetermined period. Accordingly, it is possible for the aerosol amount to easily fall in the desired range regardless of the length of the puff period of the user from the initial step (start of smoking) in which the accumulated amount in the battery 11 is sufficient up to the final step (end of smoking) in which the accumulated amount in the battery 11 is insufficient.

In the fourth modification, preferably the upper limit of the aerosol amount (desired range) atomized by the atomizer 22 is 4.0 mg per one puff action. Furthermore, preferably the upper limit is 3.0 mg per one puff action. Deterioration of the raw material pieces included in the flavor source 31A accommodated in the second cartridge 30 is suppressed by the value described above being the upper limit.

Meanwhile, preferably the lower limit of the aerosol amount (desired range) atomized by the atomizer 22 is 0.1 mg per one puff action. By setting the value described above to the lower limit, it is possible to supply the aerosol to the user at an amount that does not impart a sense of shortage, and it is possible to remove the flavor component from the flavor source 31A accommodated in the second cartridge 30 using the aerosol.

Fifth Modification

A fifth modification of the embodiment will be described below. Differences from the embodiment are mainly described below.

In the embodiment described above, the predetermined period is determined according to the standard puff period derived from statistics of the puff periods of the plurality of users. In contrast, in the fifth modification, the predetermined period is derived from statistics of the puff period of the user who actually uses the non-burning type flavor inhaler 1.

Figure 26:
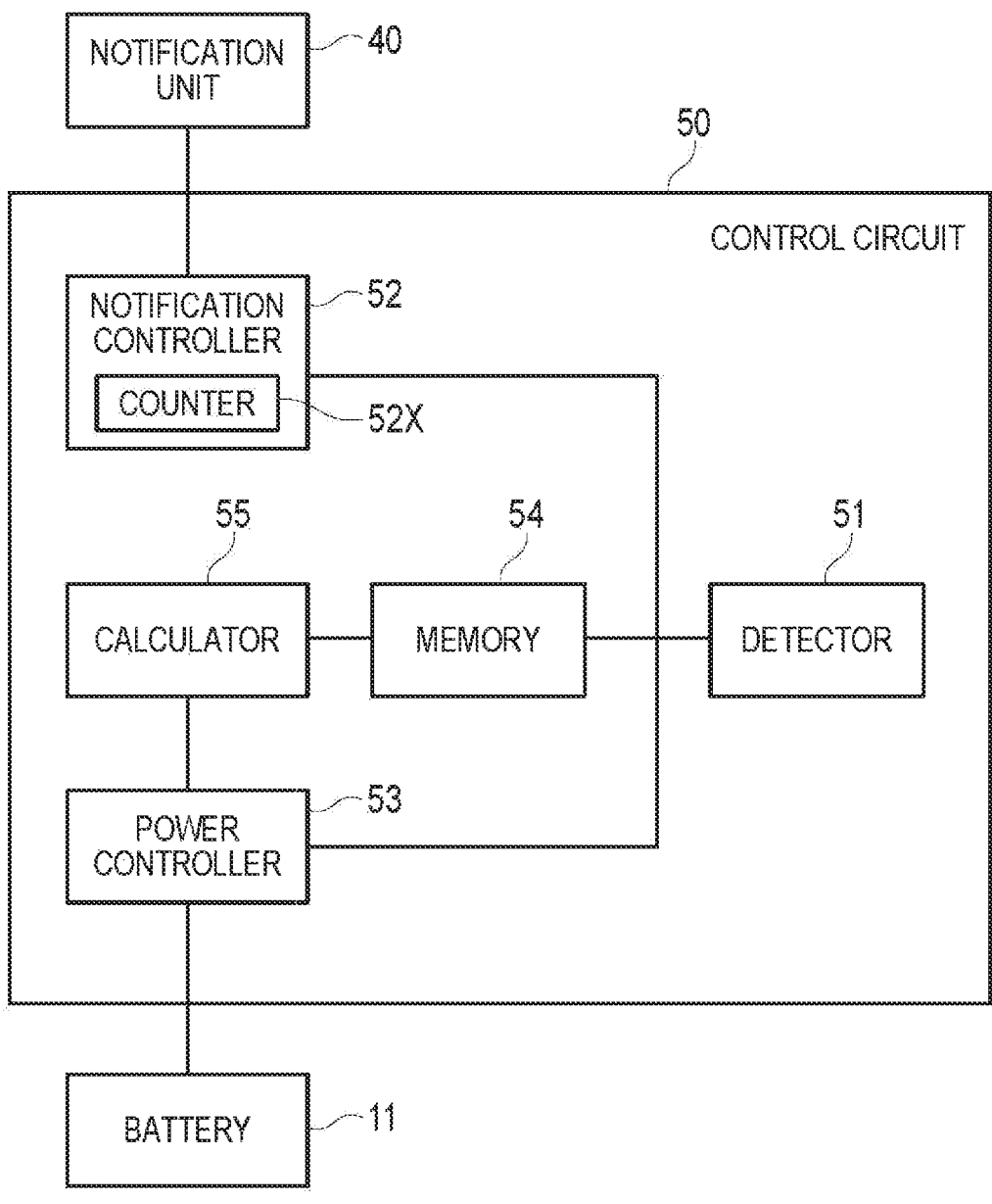
FIG. 26 is a diagram mainly illustrating a function block of a control circuit 50 according to a fifth modification.

FIG. 26 is a diagram mainly illustrating a function block of the control circuit 50 according to the fifth modification. In FIG. 26, the same reference numerals are given to the same configuration as in FIG. 15, and description of the same configuration as in FIG. 15 is omitted.

As illustrated in FIG. 26, the control circuit 50 has a memory 54 and a calculator 55 in addition to the configuration illustrated in FIG. 15.

The memory 54 stores the puff period that is a period in which the user performs the puff action.

The calculator 55 calculates the predetermined period described above from statistics of the puff period stored in the memory 54. That is, the predetermined period is derived from statistics of the puff period stored in the memory 54. However, it should be noted that the predetermined period is shorter than the upper limit of the standard puff period described above.

For example, the calculator 55 operates the predetermined period in the following procedures.

Firstly, in the same manner as in the embodiment described above, in the initial setting, the predetermined period (I seconds) is determined in advance according to the standard puff period derived from statistics of the puff periods of the plurality of users.

Secondly, for example, the average value is derived from statistics of the puff period detected in a fixed period (for example, from the start of use of the first cartridge 20 up to replacement of the first cartridge 20).

Thirdly, the predetermined period is modified to the average value (X seconds).

Fourthly, the duty ratio is modified such that the amount of power supply to the atomizer 22 during inhaling for X seconds is equal to the amount of power supply during initial setting (during inhaling for I seconds). That is, when the average value (X)<initial setting value (I), the duty ratio that corresponds to each battery voltage is relatively increased. Meanwhile, when the average value (X)>initial setting value (I), the duty ratio is reduced.

Note that, preferably for example, the predetermined period is recalculated in each fixed period (for example, replacement of the first cartridge 20).

Operation and Effect

In the fifth modification, the predetermined period is derived from statistics of the puff period of the user who actually uses the non-burning type flavor inhaler 1. Accordingly, it is possible to set a period appropriate to the user as the predetermined period referenced when stopping the power supply from the battery 11 to the atomizer 22. More particularly, it is possible to mitigate discomfort because of supply of the aerosol across the entirety of the puff period applied to the user who has a long puff period, and it is possible to increase the number of puff actions in which aerosol is supplied in the desired range to a user who has a short puff period compared to a case in which the predetermined period derived from statistics of the puff periods of a plurality of users is used by setting the predetermined period appropriate in the actual puff period of the user.

Sixth Modification

A sixth modification of the embodiment will be described below. Differences from the embodiment are mainly described below.

In the embodiment described above, the predetermined period is determined according to the standard puff period derived from statistics of the puff periods of the plurality of users. In contrast, in the sixth modification, the predetermined period is derived from statistics of the puff period of the user who actually uses the non-burning type flavor inhaler 1.

Figure 27:
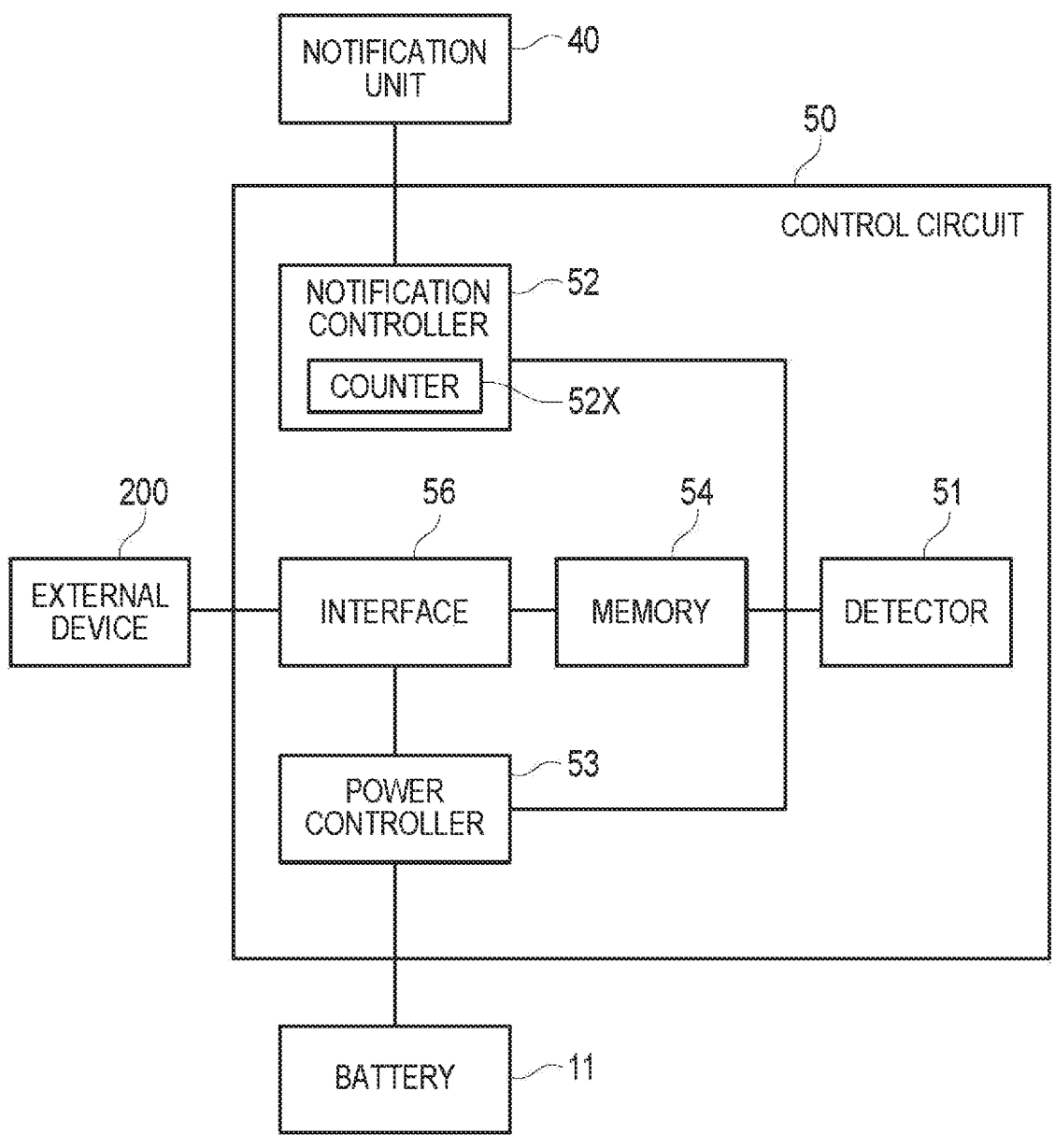
FIG. 27 is a diagram mainly illustrating a function block of a control circuit 50 according to a sixth modification.

FIG. 27 is a diagram mainly illustrating a function block of the control circuit 50 according to the sixth modification. In FIG. 27, the same reference numerals are given to the same configuration as in FIG. 15, and description of the same configuration as in FIG. 15 is omitted.

As illustrated in FIG. 27, the control circuit 50 has a memory 54 and an interface 56 in addition to the configuration illustrated in FIG. 15.

The memory 54 stores the puff period a period in which the user performs the puff action.

The interface 56 is an interface for communicating with an external device 200 provided separately from the non-burning type flavor inhaler 1. The interface 56 may be a USB port, may be a wired LAN module, may be a wireless LAN module, and may be a near field communication module (for example, Bluetooth or FeliCa). The external device 200 may be a personal computer, and may be a smartphone.

Specifically, the interface 56 transmits the puff period stored in the memory 54 to the external device 200. The interface 56 receives the predetermined period calculated from statistics from the external device 200 based on the puff period using the external device 200.

It should be noted that the external device 200 calculates the predetermined period using the same method as the calculator 55 according to the fifth modification.

Operation and Effect

In the sixth modification, the predetermined period is derived from statistics of the puff period of the user who actually uses the non-burning type flavor inhaler 1. Accordingly, it is possible to set a period appropriate to the user as the predetermined period referenced when stopping the power supply from the battery 11 to the atomizer 22. More particularly, it is possible to mitigate discomfort because of supply of the aerosol across the entirety of the puff period applied to the user who has a long puff period, and it is possible to increase the number of puff actions in which aerosol is supplied in the desired range to a user who has a short puff period compared to a case in which the predetermined period derived from statistics of the puff periods of a plurality of users is used by setting the predetermined period appropriate in the actual puff period of the user.

Seventh Modification

A seventh modification of the embodiment will be described below. Differences from the embodiment are mainly described below.

Figure 28:
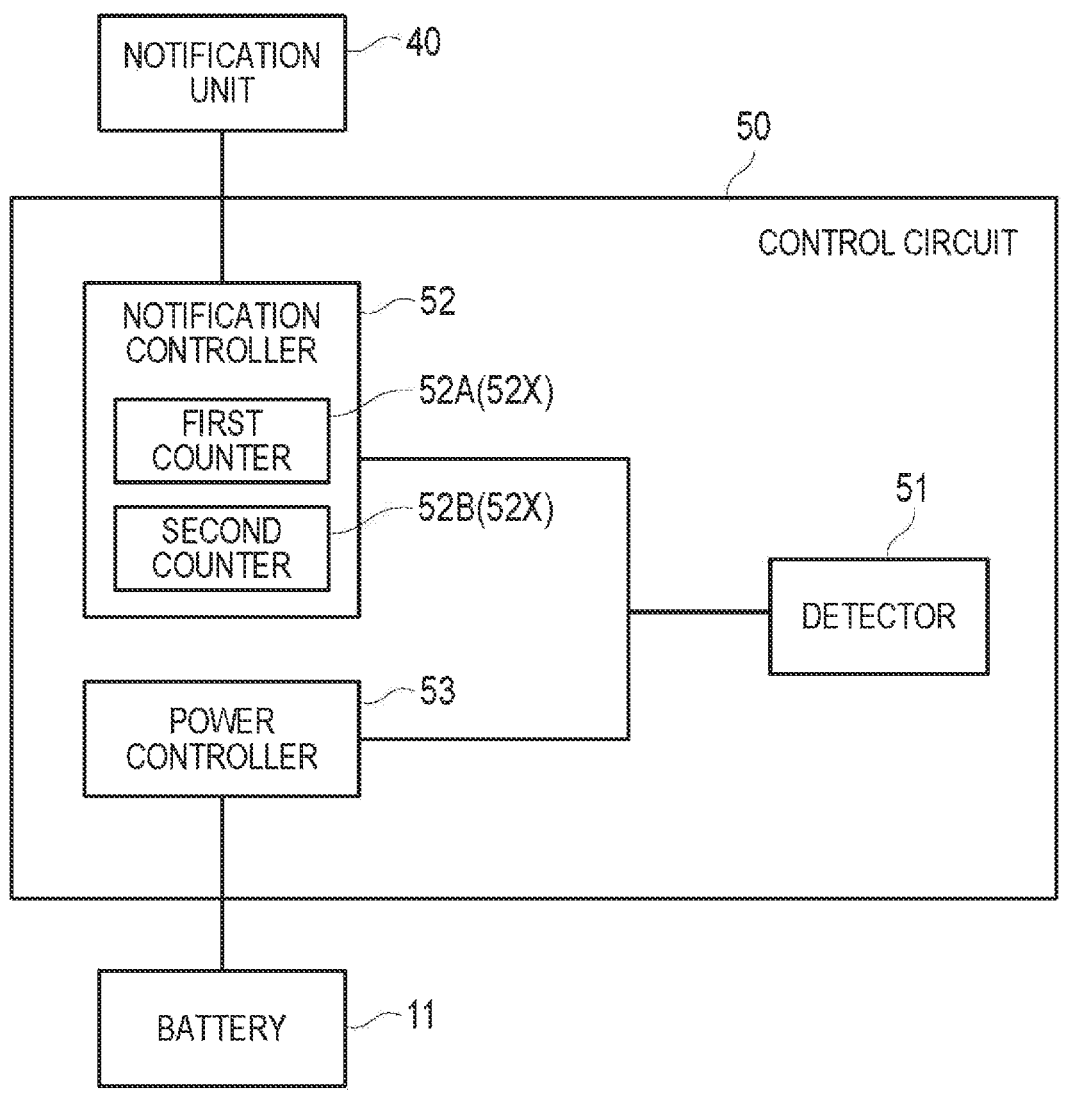
FIG. 28 is a diagram mainly illustrating a function block of a control circuit 50 according to a seventh modification.

In the embodiment described above, the notification controller 52 has the counter 52X that counts the number of puff actions or the energization time of the atomizer 22. In contrast, in the seventh modification, as illustrated in FIG. 28, the notification controller 52 has a first counter 52A and a second counter 52B as the counter 52X that counts the number of puff actions or the energization time of the atomizer 22.

In the seventh modification, it should be noted that the lifespan of the first cartridge 20 is the lifespan of the second cartridge 30×T (T is an integer)+β. Note that, β is a value smaller than the lifespan of the second cartridge 30, but is not particularly limited thereto.

The notification controller 52 detects the replacement timing of the second cartridge 30 when the count value of the first counter 52A reaches a first predetermined value. The notification controller 52 detects the replacement timing of the first cartridge 20 when the count value of the second counter 52B reaches a second predetermined value. The second predetermined value is an integral multiple of the first predetermined value.

Alternatively, when the count value of the first counter 52A reaches a predetermined value P, the notification controller 52 may detect the replacement timing of the second cartridge 30 and increment the count value of the second counter 52B. Thereby, the notification controller 52 may detect the replacement timing of the first cartridge 20 when the count value of the second counter 52B reaches a predetermined value Q. That is, in the same manner as in the embodiment described above, the notification controller 52 may detect the replacement timing of the first cartridge 20 when the number of replacement times of the second cartridge 30 reaches a predetermined number of times (predetermined value Q).

In this manner, it should be noted that as a result of the second predetermined value being an integral multiple of the first predetermined value, the notification controller 52 detects the replacement timing of the first cartridge 20 based on the number of times of replacement of the second cartridge 30.

In the seventh modification, when the count value of the first counter 52A reaches the first predetermined value, the notification controller 52 may detect the replacement timing of the second cartridge 30 and reset the count value of the first counter 52A. Alternatively, when the count value of the first counter 52A reaches the first predetermined value, the notification controller 52 may detect the replacement timing of the second cartridge 30 and reset the count value of the first counter 52A according to the predetermined operation of the user. In such a case, preferably the power controller 53 stops the power supply from the battery 11 to the atomizer 22 from the count value of the first counter 52A reaching the first predetermined value until the count value is reset.

In the seventh modification, when the count value of the second counter 52B reaches the second predetermined value, the notification controller 52 may detect the replacement timing of the first cartridge 20 and reset the count value of the second counter 52B. Alternatively, when the count value of the second counter 52B reaches the second predetermined value, the notification controller 52 may detect the replacement timing of the first cartridge 20 and reset the count value of the second counter 52B according to the predetermined operation of the user. In such a case, preferably the power controller 53 stops the power supply from the battery 11 to the atomizer 22 from the count value of the second counter 52B reaching the second predetermined value until the count value is reset.

Operation and Effect

In the seventh modification, it is possible to improve convenience for the user by notifying the replacement timing of the first cartridge 20 and the second cartridge 30 at the same timing even when replacement of the second cartridge 30 is repeated because the second predetermined value is an integral multiple of the first predetermined value.

Eighth Modification

An eighth modification of the embodiment will be described below. Differences from the embodiment are mainly described below.

Figure 29:
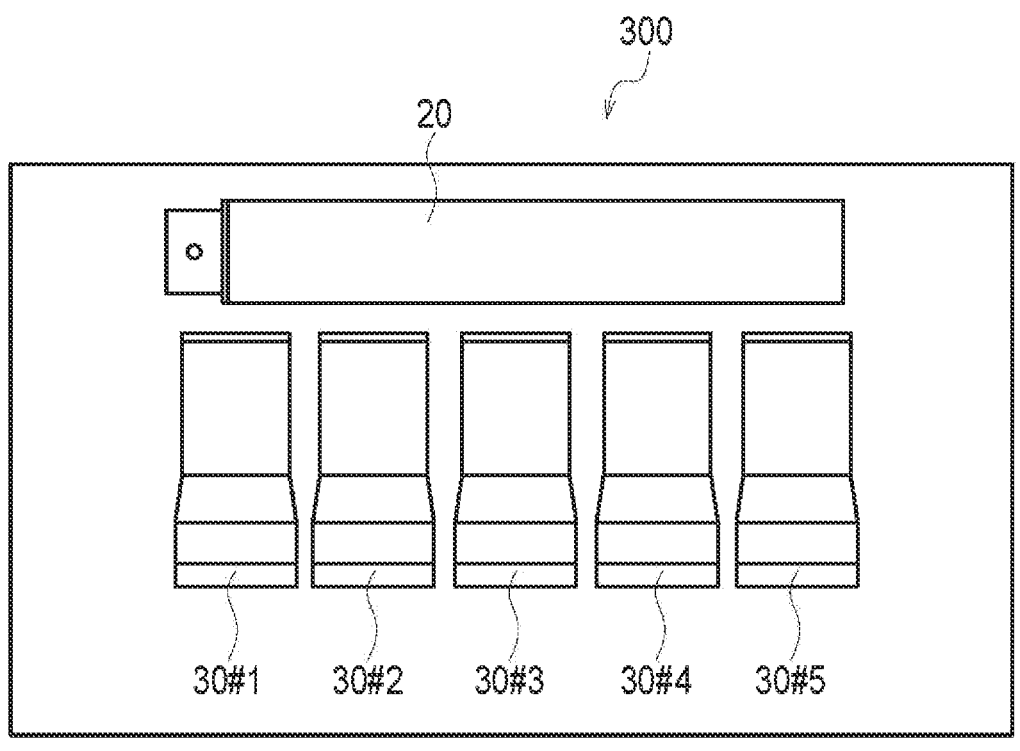
FIG. 29 is a diagram illustrating a package 300 according to an eighth modification.

In the eighth modification, a package provided with the first cartridge and the second cartridge is described. FIG. 29 is a diagram illustrating a package 300 according to the eighth modification.

As described in FIG. 29, the package 300 has the first cartridge 20 and the second cartridge 30. The number of second cartridges 30 is determined according to the lifespan of the first cartridge 20. For example, the package 300 illustrated in FIG. 29 has one first cartridge 20 and five second cartridges 30. In other words, the number of second cartridges 30 is determined such that the lifespan of one first cartridge 20 comes to an end when five second cartridges 30 are used up.

Specifically, a permissible puff number that is the number of puff actions permissible for the first cartridge 20 or a permissible energization time that is the energization time permitted in the first cartridge 20 is determined for the first cartridge 20. The number of permissible puffs and the permissible energization time are values for suppressing depletion of the aerosol source 21A. In other words, the number of permissible puffs or the permissible energization time is upper limit value allows to atomize appropriate aerosol while stably supplying the aerosol source 21A to the atomizer 22. A timing at which the number of puff actions or the energization time of the atomizer 22 reaches the predetermined value is determined as the replacement timing of the second cartridge 30. The number of second cartridges 30 is an integral part of a quotient in which the permissible puff number or the permissible energization time is divided by the predetermined value. Here, the permissible puff number or the permissible energization time may not be divided by the predetermined value. In other words, the lifespan of the first cartridge 20 may be a lifespan that has a margin with respect to the number of second cartridges 30.

Alternatively, a timing at which the number of puff actions or the energization time of the atomizer 22 reaches the first predetermined value is the replacement timing of the second cartridge 30. A timing at which the number of puff actions or the energization time of the atomizer 22 reaches the second predetermined value is the replacement timing of the first cartridge 20. The second predetermined value is an integral multiple T of the first predetermined value. The integral multiple T is the number of the second cartridges 30 that are contained in the package 300.

Operation and Effect

In the eighth modification, convenience for the user is improved since the replacement timing of the first cartridge 20 and the second cartridge 30 are aligned even when replacement of the second cartridge 30 is repeated since the number of second cartridges 30 is determined according to the lifespan of the first cartridge 20. In other words, it is possible for the user to easily ascertain the replacement timing of the first cartridge 20 by using up the second cartridge 30 contained in the package 300.

Other Embodiments

The present invention is described through the above-described embodiments, but it should not be understood that this invention is limited to the statements and the drawings constituting a part of this disclosure. From this disclosure, various alternative embodiments, examples, and operational technologies will be obvious to those skilled in the art.

In the embodiment, the first cartridge 20 has the end cap 25, but the embodiment is not limited thereto. For example, the first cartridge 20 may not have the end cap 25 when the reservoir 21 has a configuration (for example, a tank) in which it is possible to suppress leakage of the aerosol source 21A. In such a case, the aerosol flow adjustment chamber G is formed between the downstream end portion of the flow path forming body 23 and the upstream end portion of the flavor source container 31.

In the embodiment, the second cartridge 30 is accommodated in the first cartridge 20 (protruding portion 25E), but the embodiment is not limited thereto. For example, the power source unit 10 may accommodate the first cartridge 20 and the second cartridge 30. Alternatively, the first cartridge 20 and the second cartridge 30 may be connected at end surfaces to face each other. In such a case, for example, the first cartridge 20 and the second cartridge 30 are connected by screwing.

Although not particularly mentioned in the embodiment, preferably the end cap 25 is joined to the reservoir 21 to suppress refilling and the like of the aerosol source 21A in the reservoir 21.

In the embodiment, the end cap 25 has the protruding portion 25E that protrudes from the outer edge of the end cap 25 to the downstream side (flavor source container 31 side) in the cross section orthogonal to the aerosol flow path (predetermined direction A). However, the embodiment is not limited thereto. Note that, when the end cap 25 is not provided, the flow path forming body 23 may have the protruding portion 25E that protrudes from the outer edge of the flow path forming body 23 to the downstream side (flavor source container 31 side) in the cross section orthogonal to the aerosol flow path (predetermined direction A). The protruding portion 25E contacts the upstream end portion of the flavor source container 31 (for example, the outer edge of the upstream end portion).

In the embodiment, a case is exemplified in which the atomizer 22 has a heating wire (coil) wound at a predetermined pitch. However, the embodiment is not limited thereto. The shape of the heating wire forming the atomizer 22 is arbitrary.

In the embodiment, a case is exemplified in which the atomizer 22 is configured by the heating wire. However, the embodiment is not limited thereto. The atomizer 22 may atomize the aerosol source 21A using ultrasonic waves.

In the embodiment, the first cartridge 20 is replaceable. However, the embodiment is not limited thereto. Specifically, in place of the first cartridge 20, an atomizing unit that has the reservoir 21 and the atomizer 22 may be provided in the non-burning type flavor inhaler 1, and the atomizing unit may be a unit that is not replaced.

In the embodiment, the second cartridge 30 is replaceable. However, the embodiment is not limited thereto. Specifically, in place of the second cartridge 30, the flavor source unit that has the flavor source 31A may be provided in the non-burning type flavor inhaler 1, and the flavor source unit may be a unit that is not replaced. However, the second cartridge 30 is not necessarily an essential feature.

In the embodiment, the first cartridge 20 and the second cartridge 30 are replaceable. However, the embodiment is not limited thereto. Specifically, a configuration having the first cartridge 20 and the second cartridge 30 may be provided in the non-burning type flavor inhaler 1.

In the embodiment, the package 300 has one first cartridge 20. However, the embodiment is not limited thereto. The package 300 may have two or more first cartridges 20.

In the embodiment, the power controller 53 controls the amount of power supplied from the battery 11 to the atomizer 22 by pulse control. However, the embodiment is not limited thereto. The power controller 53 may control the output voltage of the battery 11. In such a case, preferably the power controller 53 modifies (or corrects) the predetermined instruction such that the aerosol amount atomized by the atomizer 22 falls within the desired range accompanying the reduction of the accumulated amount in the battery 11. Specifically, the power controller 53 may increase the instruction voltage output to the battery 11 accompanying the reduction of the accumulated amount in the battery 11 as the modification of the predetermined instruction. The modification (or correction) of the output voltage of the battery 11 is realized using, for example, a DC/DC converter. The DC/DC converter may be a step-down converter, or may be a boost converter. Note that, the power controller 53 may control both pulse control and output voltage such that the aerosol amount atomized by the atomizer 22 falls within the desired range.

In the embodiment, the power controller 53 increases the duty ratio output to the battery 11 in one puff action accompanying the reduction of the accumulated amount in the battery 11 as the modification of the predetermined instruction. However, the embodiment is not limited thereto. The power controller 53 may extend the predetermined period for stopping power supply from the battery 11 to the atomizer 22 accompanying the reduction of the accumulated amount in the battery 11 as the modification of the predetermined instruction.

In the embodiment, the detector 51 is connected to a voltage sensor provided on a sensor line that connects the battery 11 and the atomizer 22, and detects power supply based on the output result of the voltage sensor. However, the embodiment is not limited thereto. For example, the detector 51 may be connected to a current sensor provided on the sensor line that connects the battery 11 and the atomizer 22, and may detect power supply based on the output result of the current sensor.

In the embodiment, the power controller 53 instructs, to the battery 11, output of power to the atomizer 22 in the puff period in which the puff action is performed, but does not instruct, to the battery 11, output of power to the atomizer 22 in the non-puff period in which the puff action is not performed. However, the embodiment is not limited thereto. The power controller 53 may switch power output to the atomizer 22 according to the operation of the hardware interface (for example, the switch or the button) for performing power output to the atomizer 22. That is, the puff action and the non-puff action are switched according to the operation of the hardware interface.

In the embodiment, the notification controller 52 controls the notification unit 40 to notify various information. For example, the notification controller 52 controls the notification unit 40 to notify a replacement timing of the second cartridge 30 according to detection of the replacement timing of the second cartridge 30. However, the embodiment is not limited thereto. Specifically, the notification controller 52 may control the notification unit 40 (here, a light emitting element such as an LED, hereinafter the same) in a first light-emitting mode (predetermined mode) in the puff period in which the puff action is performed. In addition, the notification controller 52 may control the notification unit 40 in a second light-emitting mode that is different from the first light-emitting mode in the non-puff period in which the puff action is not performed. Note that, the first light-emitting mode (predetermined mode) may at least not include an extinction mode, may be a lit-up mode, and may be a blinking mode. The second light-emitting mode at least may be different from the first light-emitting mode (predetermined mode), and may include the extinction mode.

Here, the puff period described above may not be a power supply state to the atomizer 22 described above, and preferably is determined according to the output result of the inhalation sensor connected to the detector 51 described above. Accordingly, as described above, when the predetermined period from the start of power supply to the atomizer 22 has elapsed, even in a case in which the power controller 53 stops power supply from the battery 11 to the atomizer 22, and when the puff action continues, the notification controller 52 controls the notification unit 40 in the first light-emitting mode (predetermined mode). In this manner, it is possible to impart to the user an impression that the operation of the non-burning type flavor inhaler 1 is linked to the puff action of the user by linking the light-emitting mode of the notification unit 40 that tends to be recognized by the user not in the power supply state of the atomizer 22 in the detection result of the inhalation sensor while controlling such that the aerosol amount atomized by the atomizer 22 falls within the desired range by stopping the power supply to the atomizer 22 accompanying the passage of the predetermined period.

Note that, the light-emitting mode is defined according to a combination of parameters such as the amount of light of the light-emitting element, the number of the light-emitting elements that are in the lit-up state, the color of the light-emitting element, the cycle of repetition of lighting up of the light-emitting element and lighting out of the light-emitting element, etc. A different light-emitting mode implies a light-emitting mode in which any one of the parameters described above is different.

In addition, the puff period in which the puff action is performed by the user may be determined by the operation of the hardware interface (for example, the switch or the button) for controlling the power supply to the atomizer 22 without the output result of the inhalation sensor connected to the detector 51 described above.

INDUSTRIAL APPLICABILITY

According to the present invention, it is possible to provide the non-burning type flavor inhaler and the control method that can fall the aerosol amount supplied per one puff action in the desired range through the puff action from the start of smoking (the initial stage in which an accumulated amount in a battery is sufficient) until the end of smoking (that is, the final stage in which the accumulated amount in the battery decreases), regardless of the length of a puff period of the user and the accumulated amount in the battery.

The invention claimed is:
1. A non-combustible inhaler comprising:
an atomizer configured to atomize an aerosol source;

a battery configured to accumulate power to be supplied to the atomizer;
a sensor configured to detect a puff action; and
circuitry configured to
detect that a puff action has occurred based on an output of the sensor;
identify, in a case of detecting the puff action, a duty ratio for suppling pulse-width-modulated power to the atomizer based on a remaining amount of power of the battery;
initiate supplying pulse-width-modulated power from the battery to the atomizer at a first duty ratio in a case that it is detected that the puff action has occurred and the remaining amount of power of the battery is a first value;
initiate supplying the pulse-width-modulated power from the battery to the atomizer at a second duty ratio, which is different from the first duty ratio, in a case that it is detected that the puff action has occurred and the remaining amount of power of the battery is a second value, which is different from the first value; and
stop supplying the pulse-width-modulated power from the battery to the atomizer after a predetermined time has elapsed from initiating supplying the pulse-width-modulated power from the battery to the atomizer, wherein
the circuitry is configured to acquire an upper limit time value based on stored data indicating a plurality of puff actions previously performed by at least one of a plurality of users of the non-combustible inhaler, and
the predetermined time is a time that is less than the acquired upper limit time value of the puff period, wherein
the circuitry is configured to store puff period data from puff actions performed by the at least one of the plurality of users, derive the upper limit time value from statistics of the stored puff period data, and set the predetermined time based on the derived upper limit time value.
2. The non-combustible inhaler of claim 1, wherein the first duty ratio is lower than the second duty ratio and the first value is greater than the second value.
3. The non-combustible inhaler of claim 1, wherein the circuitry is configured to control the duty ratio of the pulse-width-modulated power supplied from the battery to the atomizer to increase as the remaining amount of power of the battery decreases.
4. The non-combustible inhaler of claim 1, wherein the circuitry is configured to control the duty ratio of the pulse-width-modulated power supplied from the battery to the atomizer to continuously increase as the remaining amount of power of the battery decreases during a time after initiating supplying the pulse-width-modulated power from the battery to the atomizer and before stopping supplying the pulse-width-modulated power from the battery to the atomizer.
5. The non-combustible inhaler of claim 1, wherein the circuitry is configured to control the duty ratio of the pulse-width-modulated power supplied from the battery to the atomizer to change according to a predetermined rate corresponding to the remaining amount of power of the battery.
6. The non-combustible inhaler of claim 1, wherein the atomizer is configured to atomize the aerosol source without burning.
7. The non-combustible inhaler of claim 1, further comprising:

a housing including a first electrical connector configured to be detachably connected to the atomizer.

8. The non-combustible inhaler of claim 7, wherein the battery, the sensor and the circuitry are included in the housing.

9. The non-combustible inhaler of claim 8, further comprising:
a cartridge including the atomizer and a reservoir configured to store the aerosol source.

10. The non-combustible inhaler of claim 9, wherein the cartridge includes a second electrical connector configured to be detachably connected to the first electrical connector of the housing.

11. The non-combustible inhaler of claim 1, further comprising:
a light emitting diode (LED) configured to output a notification to a user of the non-combustible inhaler.

12. The non-combustible inhaler of claim 11, further comprising:
a housing including the battery, the sensor, the circuitry, the LED, and a first electrical connector configured to be detachably connected to the atomizer.

13. The non-combustible inhaler of claim 11, wherein the circuitry is configured to control the LED to output a predetermined notification to the user of the non-combustible inhaler upon detecting that the puff action has occurred based on the output of the sensor.

14. The non-combustible inhaler of claim 11, wherein the circuitry is configured to control the LED to output a predetermined notification to the user of the non-combustible inhaler upon initiating supplying the pulse-width-modulated power from the battery to the atomizer.

15. The non-combustible inhaler of claim 11, wherein the controller is configured to control the LED to output a predetermined notification to the user of the non-combustible inhaler in a case that it is determined that a remaining amount of power of the battery is below a threshold value.

16. The non-combustible inhaler of claim 11, wherein the circuitry is configured to:
determine that the battery is in a low power state based on a measured output voltage of the battery; and
control the LED to output a predetermined notification in a case it is determined that the battery is in the low power state.

17. The non-combustible inhaler of claim 1, wherein the circuitry is configured to stop supplying the pulse-width modulated power from the battery to the atomizer after the predetermined time has elapsed from initiating supply of the pulse with-modulated power from the battery to the atomizer regardless of whether the puff action is maintained.

18. A non-combustible inhaler comprising:
an atomizer configured to atomize an aerosol source;
a battery configured to accumulate power to be supplied to the atomizer;
a sensor configured to detect a puff action; and
circuitry configured to
identify that a puff action has occurred based on an output of the sensor;
initiate supplying pulse-width-modulated power from the battery to the atomizer at a first duty ratio in a case that it is detected that the puff action has occurred and remaining amount of power of the battery is a first value;

initiate supplying the pulse-width-modulated power from the battery to the atomizer at a second duty ratio, which is different from the first duty ratio, in a case that it is detected that the puff action has occurred and the remaining amount of power of the battery is a second value, which is different from the first value; and
stop supplying pulse-width-modulated power from the battery to the atomizer after a predetermined time has elapsed from initiating supplying the pulse-width-modulated power from the battery to the atomizer, wherein
the circuitry is configured to acquire an upper limit time value based on stored data indicating a plurality of puff actions previously performed by at least one of a plurality of users of the non-combustible inhaler, and
the predetermined time is a time that is less than the acquired upper limit time value of the puff period, wherein
the circuitry is configured to store puff period data from puff actions performed by the at least one of the plurality of users, derive the upper limit time value from statistics of the stored puff period data, and set the predetermined time based on the derived upper limit time value.

19. A non-combustible inhaler comprising:
an atomizer configured to atomize an aerosol source;
a battery configured to accumulate power to be supplied to the atomizer;
a sensor configured to detect a puff action; and
circuitry configured to
detect that a puff action has occurred based on an output of the sensor;
identify, in a case of detecting the puff action, a duty ratio for suppling pulse-width-modulated power to the atomizer based on a remaining amount of power of the battery;
initiate supplying pulse-width-modulated power from the battery to the atomizer at a first duty ratio in a case that it is detected that the puff action has occurred and the remaining amount of power of the battery is above a threshold value;
initiate supplying the pulse-width-modulated power from the battery to the atomizer at a second duty ratio, which is higher than the first duty ratio, in a case that it is detected that the puff action has occurred and the remaining amount of power of the battery is below the threshold value; and
stop supplying the pulse-width-modulated power from the battery to the atomizer after a predetermined time has elapsed from initiating supplying the pulse-width-modulated power from the battery to the atomizer, wherein
the circuitry is configured to acquire an upper limit time value based on stored data indicating a plurality of puff actions previously performed by at least one of a plurality of users of the non-combustible inhaler, and
the predetermined time is a time that is less than the acquired upper limit time value of the puff period, wherein
the circuitry is configured to store puff period data from puff actions performed by the at least one of the plurality of users, derive the upper limit time value from statistics of the stored puff period data, and set the predetermined time based on the derived upper limit time value.

* * * * *